(12) United States Patent
Hamersky et al.

(10) Patent No.: US 11,666,514 B2
(45) Date of Patent: Jun. 6, 2023

(54) FIBROUS STRUCTURES CONTAINING POLYMER MATRIX PARTICLES WITH PERFUME INGREDIENTS

(71) Applicant: The Procter & Gamble Company, Cincinnati, OH (US)

(72) Inventors: Mark William Hamersky, Hamilton, OH (US); Jennifer Elaine Hilvert, Cincinnati, OH (US); Andreas Josef Dreher, Cincinnati, OH (US); Stephen Robert Glassmeyer, Cincinnati, OH (US); Emily Lao Hickey, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/577,120

(22) Filed: Sep. 20, 2019

(65) Prior Publication Data

US 2020/0093710 A1    Mar. 26, 2020

Related U.S. Application Data

(60) Provisional application No. 62/734,312, filed on Sep. 21, 2018.

(51) Int. Cl.
*A61K 8/02* (2006.01)
*A61K 8/81* (2006.01)
*A61Q 5/02* (2006.01)
*A61Q 5/12* (2006.01)
*A61K 8/41* (2006.01)

(52) U.S. Cl.
CPC ............ *A61K 8/027* (2013.01); *A61K 8/0208* (2013.01); *A61K 8/0275* (2013.01); *A61K 8/416* (2013.01); *A61K 8/817* (2013.01); *A61K 8/8158* (2013.01); *A61Q 5/02* (2013.01); *A61Q 5/12* (2013.01); *A61K 2800/412* (2013.01); *A61K 2800/54* (2013.01); *A61K 2800/56* (2013.01); *A61K 2800/77* (2013.01); *A61K 2800/87* (2013.01)

(58) Field of Classification Search
CPC ...... A61K 8/027; A61K 8/8158; A61K 8/817; A61K 8/0275; A61K 8/416; A61K 8/0208; A61K 2800/54; A61K 2800/77; A61K 2800/87; A61K 2800/56; A61K 2800/412; A61Q 5/02; A61Q 5/12
See application file for complete search history.

(56) References Cited

U.S. PATENT DOCUMENTS

| 1,421,350 A | 6/1922 | Powell |
| 2,356,168 A | 8/1944 | Mabley |

(Continued)

FOREIGN PATENT DOCUMENTS

| AU | 2004202461 B2 | 11/2007 |
| CA | 2524099 A1 | 4/2006 |

(Continued)

OTHER PUBLICATIONS

All final and non-final office actions for U.S. Appl. No. 16/431,028.

(Continued)

*Primary Examiner* — Hong Yu
(74) *Attorney, Agent, or Firm* — Alexandra S. Anoff

(57) ABSTRACT

A fibrous structure with a plurality of fibrous elements and agglomerated particles. The agglomerated particles can be matrix particles containing perfume.

20 Claims, 13 Drawing Sheets

(56) References Cited

U.S. PATENT DOCUMENTS

| | | |
|---|---|---|
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,613,185 A | 10/1952 | Marshall |
| 2,658,072 A | 11/1953 | Milton |
| 2,694,668 A | 11/1954 | Fricke |
| 2,809,971 A | 10/1957 | Jack et al. |
| 3,152,046 A | 10/1964 | Maria |
| 3,236,733 A | 2/1966 | Karsten et al. |
| 3,293,718 A | 12/1966 | Melvin |
| 3,321,425 A | 5/1967 | Karl-ludwig et al. |
| 3,332,880 A | 7/1967 | Adriaan et al. |
| 3,426,440 A | 2/1969 | Shen et al. |
| 3,428,478 A | 2/1969 | Donaldson et al. |
| 3,463,308 A | 8/1969 | Deneke |
| 3,489,688 A | 1/1970 | Pospischil |
| 3,570,122 A | 3/1971 | Willimas |
| 3,589,007 A | 6/1971 | Walton |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,859,125 A | 1/1975 | Miller |
| 3,875,300 A | 4/1975 | Homm et al. |
| 3,929,678 A | 12/1975 | Laughlin |
| 3,957,921 A | 5/1976 | Iwahashi et al. |
| 3,967,921 A | 7/1976 | Haberli et al. |
| 4,020,156 A | 4/1977 | Murray et al. |
| 4,024,078 A | 5/1977 | Gilbert et al. |
| 4,051,081 A | 9/1977 | Jabs et al. |
| 4,089,945 A | 5/1978 | Brinkman et al. |
| 4,149,551 A | 4/1979 | Benjamin et al. |
| 4,185,125 A | 1/1980 | Kimura et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,286,016 A | 8/1981 | Dimond |
| 4,315,965 A | 2/1982 | Mason |
| 4,323,525 A | 4/1982 | Bornat |
| 4,323,683 A | 4/1982 | Bolich, Jr. et al. |
| 4,340,583 A | 7/1982 | Wason |
| 4,342,813 A | 8/1982 | Erickson |
| 4,345,080 A | 8/1982 | Bolich, Jr. |
| D266,829 S | 11/1982 | Yoshizawa et al. |
| 4,377,615 A | 3/1983 | Suzuki |
| 4,379,753 A | 4/1983 | Bolich, Jr. |
| 4,381,919 A | 5/1983 | Jacquet et al. |
| 4,415,617 A | 11/1983 | Elia |
| 4,422,853 A | 12/1983 | Jacquet et al. |
| 4,448,699 A | 5/1984 | Barrat et al. |
| 4,470,982 A | 9/1984 | Winkler |
| 4,507,280 A | 3/1985 | Pohl et al. |
| 4,529,586 A | 7/1985 | De Marco et al. |
| 4,536,361 A | 8/1985 | Torobin |
| 4,565,647 A | 1/1986 | Llenado |
| D286,450 S | 10/1986 | Tovey |
| 4,635,351 A | 1/1987 | Koch et al. |
| 4,639,390 A | 1/1987 | Shoji |
| 4,663,158 A | 5/1987 | Wolfram et al. |
| 4,710,374 A | 12/1987 | Grollier et al. |
| 4,723,362 A | 2/1988 | Boerger |
| 4,727,410 A | 2/1988 | Higgins, III |
| 4,822,613 A | 4/1989 | Rodero |
| 4,885,107 A | 12/1989 | Wetzel |
| 4,892,758 A | 1/1990 | Serbiak |
| 4,976,953 A | 12/1990 | Orr et al. |
| 4,990,280 A | 2/1991 | Thorengaard |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,102,129 A | 4/1992 | Roberts |
| 5,104,646 A | 4/1992 | Bolich, Jr. |
| 5,106,609 A | 4/1992 | Bolich, Jr. |
| 5,166,276 A | 11/1992 | Hayama et al. |
| D334,420 S | 3/1993 | Copeland et al. |
| 5,220,033 A | 6/1993 | Kamei et al. |
| 5,230,853 A | 7/1993 | Colegrove |
| 5,261,426 A | 11/1993 | Kellett et al. |
| 5,280,079 A | 1/1994 | Allen et al. |
| RE34,584 E | 4/1994 | Grote et al. |
| D351,345 S | 10/1994 | Geho |
| 5,364,627 A | 11/1994 | Song |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee |
| 5,429,628 A | 7/1995 | Trinh et al. |
| 5,444,113 A | 8/1995 | Sinclair et al. |
| 5,455,114 A | 10/1995 | Ohmory |
| 5,457,895 A | 10/1995 | Thompson et al. |
| 5,458,433 A | 10/1995 | Stastny |
| 5,470,424 A | 11/1995 | Isaac |
| 5,476,597 A | 12/1995 | Sakata et al. |
| 5,501,238 A | 3/1996 | Von Borstel et al. |
| 5,533,636 A | 7/1996 | Reiker |
| 5,538,735 A | 7/1996 | Ahn |
| 5,580,481 A | 12/1996 | Sakata et al. |
| 5,582,786 A | 12/1996 | Brunskill et al. |
| D378,180 S | 2/1997 | Hayes |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,716,692 A | 2/1998 | Warner |
| 5,750,122 A | 5/1998 | Evans |
| 5,780,047 A | 7/1998 | Kamiya et al. |
| 5,780,418 A | 7/1998 | Niinaka |
| D398,847 S | 9/1998 | Wyslotsky |
| D399,260 S | 10/1998 | Thimote |
| 5,849,378 A | 12/1998 | Gask |
| 5,879,493 A | 3/1999 | Johnson |
| D407,640 S | 4/1999 | Crapser et al. |
| D408,223 S | 4/1999 | Henry |
| 5,911,224 A | 6/1999 | Berger |
| 5,925,603 A | 7/1999 | D Angelo |
| 5,955,419 A | 9/1999 | Barket, Jr. et al. |
| D416,103 S | 11/1999 | Hashmi |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon et al. |
| 6,028,016 A | 2/2000 | Yahiaoui et al. |
| 6,029,808 A | 2/2000 | Peck et al. |
| 6,034,043 A | 3/2000 | Fujiwara |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer et al. |
| D441,869 S | 5/2001 | Bloor et al. |
| D442,353 S | 5/2001 | Macias |
| D442,739 S | 5/2001 | Friesenhahn |
| D443,389 S | 6/2001 | Friesenhahn |
| D448,802 S | 10/2001 | Lariviere, Jr. et al. |
| D449,881 S | 10/2001 | Mock, Sr. |
| D450,378 S | 11/2001 | Minakuchi et al. |
| 6,319,510 B1 | 11/2001 | Yates |
| 6,365,142 B1 | 4/2002 | Tamura |
| 6,382,526 B1 | 5/2002 | Reneker et al. |
| 6,420,625 B1 | 7/2002 | Jones |
| 6,440,926 B1 | 8/2002 | Spadoni et al. |
| D462,900 S | 9/2002 | Yamada et al. |
| 6,448,462 B2 | 9/2002 | Groitzsch |
| 6,458,754 B1 | 10/2002 | Velazquez et al. |
| D465,303 S | 11/2002 | Friesenhahn |

(56) References Cited

U.S. PATENT DOCUMENTS

| | | |
|---|---|---|
| 6,503,521 B1 | 1/2003 | Atis et al. |
| 6,525,034 B2 | 2/2003 | Dalrymple et al. |
| 6,552,123 B1 | 4/2003 | Katayama |
| D479,561 S | 9/2003 | Meyer |
| 6,623,694 B1 | 9/2003 | Ferguson et al. |
| D484,749 S | 1/2004 | Garraway |
| 6,723,160 B2 | 4/2004 | Mackey et al. |
| D489,162 S | 5/2004 | Dings-plooij |
| 6,790,814 B1 | 9/2004 | Marin |
| 6,800,295 B2 | 10/2004 | Fox |
| 6,802,295 B2 | 10/2004 | Bedwell et al. |
| 6,808,375 B2 | 10/2004 | Kloetzer |
| 6,825,161 B2 | 11/2004 | Shefer et al. |
| 6,831,046 B2 | 12/2004 | Carew et al. |
| 6,846,784 B2 | 1/2005 | Engel |
| 6,878,368 B2 | 4/2005 | Ohta et al. |
| D509,935 S | 9/2005 | Burt |
| 6,943,200 B1 | 9/2005 | Corrand et al. |
| D515,915 S | 2/2006 | Karim |
| 7,015,181 B2 | 3/2006 | Lambino |
| 7,041,369 B1 | 5/2006 | Mackey et al. |
| 7,115,551 B2 | 10/2006 | Hasenoehrl |
| 7,169,740 B2 | 1/2007 | Sommerville-Roberts |
| RE39,557 E | 4/2007 | Moe |
| 7,208,460 B2 | 4/2007 | Shefer et al. |
| D549,051 S | 8/2007 | Nordwall |
| 7,285,520 B2 | 10/2007 | Krzysik |
| 7,291,300 B2 | 11/2007 | Chhabra et al. |
| 7,387,787 B2 | 6/2008 | Fox |
| D576,753 S | 9/2008 | Mukai |
| D577,332 S | 9/2008 | Moore |
| 7,429,273 B2 | 9/2008 | De |
| D578,881 S | 10/2008 | Friedland |
| D588,332 S | 3/2009 | Phelan |
| 7,507,698 B2 | 3/2009 | Franzolin |
| 7,704,328 B2 | 4/2010 | Bailey et al. |
| 7,832,552 B2 | 11/2010 | Newman |
| 7,846,462 B2 | 12/2010 | Spadini et al. |
| 7,892,992 B2 | 2/2011 | Kamada et al. |
| 7,901,696 B2 | 3/2011 | Eknoian et al. |
| D640,921 S | 7/2011 | Caldwell |
| D644,541 S | 9/2011 | Schrader et al. |
| D651,096 S | 12/2011 | Nakagiri |
| D655,154 S | 3/2012 | Amos |
| 8,197,830 B2 | 6/2012 | Heifman et al. |
| 8,268,764 B2 | 9/2012 | Glenn, Jr. et al. |
| 8,273,333 B2 | 9/2012 | Glenn, Jr. et al. |
| 8,288,332 B2 | 10/2012 | Fossum et al. |
| 8,309,505 B2 | 11/2012 | Fossum et al. |
| 8,349,232 B2 | 1/2013 | Pourdeyhimi |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| 8,367,596 B2 | 2/2013 | Fossum et al. |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. et al. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,541,081 B1 | 9/2013 | Ranganathan et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. |
| 8,785,361 B2 | 7/2014 | Sivik |
| D712,159 S | 9/2014 | Clerici et al. |
| D712,822 S | 9/2014 | Brusaw et al. |
| 8,980,816 B2 | 3/2015 | Dreher |
| 9,062,186 B2 | 6/2015 | Longdon et al. |
| D739,227 S | 9/2015 | Mitchell et al. |
| D740,928 S | 10/2015 | Bruining et al. |
| 9,163,205 B2 | 10/2015 | Sivik et al. |
| 9,175,250 B2 | 11/2015 | Sivik et al. |
| 9,198,838 B2 | 12/2015 | Glenn, Jr. |
| D748,240 S | 1/2016 | Goode |
| 9,421,153 B2 | 8/2016 | Sivik et al. |
| D769,522 S | 10/2016 | Venet |
| D771,788 S | 11/2016 | Duckwitz |
| 9,480,628 B2 | 11/2016 | Sivik et al. |
| D774,086 S | 12/2016 | Montes et al. |
| D775,198 S | 12/2016 | Montes et al. |
| 9,539,444 B2 | 1/2017 | Kinoshita et al. |
| 9,545,364 B2 | 1/2017 | Glenn, Jr. et al. |
| D778,026 S | 2/2017 | Roetheli |
| D793,025 S | 8/2017 | Slusarczyk et al. |
| D797,551 S | 9/2017 | Chatterton |
| D798,143 S | 9/2017 | Chatterton |
| D808,583 S | 1/2018 | Zietek |
| D811,922 S | 3/2018 | Lefave |
| D811,935 S | 3/2018 | Hughes |
| D819,836 S | 6/2018 | Noïl |
| D848,102 S | 5/2019 | Carlson et al. |
| D850,041 S | 5/2019 | Endle |
| 10,294,586 B2 | 5/2019 | Sivik et al. |
| D851,344 S | 6/2019 | Carlson et al. |
| D857,156 S | 8/2019 | Hani |
| D857,242 S | 8/2019 | Darrow et al. |
| D857,929 S | 8/2019 | Darrow et al. |
| D862,020 S | 10/2019 | Gorrell et al. |
| D863,600 S | 10/2019 | Chao |
| D864,507 S | 10/2019 | Stoughton et al. |
| D866,105 S | 11/2019 | Carlson et al. |
| D866,891 S | 11/2019 | Carlson et al. |
| D866,892 S | 11/2019 | Hunt et al. |
| D866,893 S | 11/2019 | Hunt et al. |
| D867,717 S | 11/2019 | Chavez |
| D868,159 S | 11/2019 | Swisher et al. |
| D868,953 S | 12/2019 | Mckendree |
| 10,569,286 B2 | 2/2020 | Anderson et al. |
| D878,694 S | 3/2020 | Carlson et al. |
| 10,646,413 B2 | 5/2020 | Sivik et al. |
| D901,115 S | 11/2020 | Carlson et al. |
| D903,152 S | 11/2020 | Chao |
| 10,821,056 B2 | 11/2020 | Swartz et al. |
| D906,802 S | 1/2021 | Chi |
| 10,894,005 B2 | 1/2021 | Sivik et al. |
| D910,434 S | 2/2021 | Tan et al. |
| D910,457 S | 2/2021 | Lee |
| D921,166 S | 6/2021 | Meyers |
| D933,095 S | 10/2021 | Heiner et al. |
| 11,351,094 B2 | 6/2022 | Hamersky et al. |
| 11,395,789 B2 | 7/2022 | Pratt et al. |
| 2001/0037851 A1 | 11/2001 | Mortellite |
| 2002/0044968 A1 | 4/2002 | Van Lengerich |
| 2002/0064510 A1 | 5/2002 | Dalrymple et al. |
| 2002/0077264 A1 | 6/2002 | Roberts et al. |
| 2002/0081732 A1 | 6/2002 | Bowlin et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0161088 A1 | 10/2002 | Kochvar |
| 2002/0173213 A1 | 11/2002 | Chu |
| 2002/0175449 A1 | 11/2002 | Chu et al. |
| 2002/0177621 A1 | 11/2002 | Hanada et al. |
| 2002/0187181 A1 | 12/2002 | Godbey et al. |
| 2003/0013369 A1 | 1/2003 | Soane et al. |
| 2003/0017208 A1 | 1/2003 | Ignatious |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan et al. |
| 2003/0099691 A1 | 5/2003 | Lydzinski et al. |
| 2003/0099692 A1 | 5/2003 | Lydzinski et al. |
| 2003/0114332 A1 | 6/2003 | Ramcharan et al. |
| 2003/0141662 A1 | 7/2003 | Kost et al. |
| 2003/0166489 A1 | 9/2003 | Van Asten et al. |
| 2003/0166495 A1 | 9/2003 | Wang |
| 2003/0180242 A1 | 9/2003 | Eccard et al. |
| 2003/0185872 A1 | 10/2003 | Kochinke |

(56) References Cited

U.S. PATENT DOCUMENTS

| | | |
|---|---|---|
| 2003/0186826 A1 | 10/2003 | Eccard et al. |
| 2003/0194416 A1 | 10/2003 | Shefer |
| 2003/0199412 A1 | 10/2003 | Gupta |
| 2003/0207776 A1 | 11/2003 | Shefer et al. |
| 2003/0209166 A1 | 11/2003 | Vanmaele et al. |
| 2003/0215522 A1 | 11/2003 | Johnson et al. |
| 2003/0224959 A1 | 12/2003 | Smith |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott |
| 2004/0053808 A1 | 3/2004 | Raehse et al. |
| 2004/0059055 A1 | 3/2004 | Inada |
| 2004/0071742 A1 | 4/2004 | Popplewell |
| 2004/0071755 A1 | 4/2004 | Fox |
| 2004/0082239 A1 | 4/2004 | Di et al. |
| 2004/0108615 A1 | 6/2004 | Foley |
| 2004/0110656 A1 | 6/2004 | Casey et al. |
| 2004/0118852 A1 | 6/2004 | Barmore et al. |
| 2004/0126585 A1 | 7/2004 | Kerins et al. |
| 2004/0170836 A1 | 9/2004 | Bond |
| 2004/0175404 A1 | 9/2004 | Shefer |
| 2004/0180597 A1 | 9/2004 | Kamada |
| 2004/0202632 A1 | 10/2004 | Gott et al. |
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2004/0253434 A1 | 12/2004 | Patel |
| 2005/0003048 A1 | 1/2005 | Pearce |
| 2005/0003991 A1 | 1/2005 | Macquarrie |
| 2005/0008776 A1 | 1/2005 | Chhabra |
| 2005/0069575 A1 | 3/2005 | Fox |
| 2005/0118237 A1 | 6/2005 | Krzysik et al. |
| 2005/0136772 A1 | 6/2005 | Chen et al. |
| 2005/0136780 A1 | 6/2005 | Clark et al. |
| 2005/0137115 A1 | 6/2005 | Cole et al. |
| 2005/0137272 A1 | 6/2005 | Gaserod |
| 2005/0159730 A1 | 7/2005 | Kathrani et al. |
| 2005/0180962 A1 | 8/2005 | Raz et al. |
| 2005/0202992 A1 | 9/2005 | Grandio Portabales et al. |
| 2005/0209574 A1 | 9/2005 | Boehringer |
| 2005/0220745 A1 | 10/2005 | Lu |
| 2005/0232954 A1 | 10/2005 | Yoshinari et al. |
| 2005/0267005 A1 | 12/2005 | Dasque et al. |
| 2005/0272836 A1 | 12/2005 | Yaginuma et al. |
| 2005/0281757 A1 | 12/2005 | Ibrahim |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0083784 A1 | 4/2006 | Ignatious |
| 2006/0128592 A1 | 6/2006 | Ross |
| 2006/0134412 A1 | 6/2006 | Mackey |
| 2006/0159730 A1 | 7/2006 | Simon |
| 2006/0160453 A1 | 7/2006 | Suh |
| 2006/0228319 A1 | 10/2006 | Vona, Jr. et al. |
| 2006/0274263 A1 | 12/2006 | Yacktman et al. |
| 2007/0028939 A1 | 2/2007 | Mareri et al. |
| 2007/0054579 A1 | 3/2007 | Baker, Jr |
| 2007/0098749 A1 | 5/2007 | Eknoian et al. |
| 2007/0099813 A1 | 5/2007 | Luizzi |
| 2007/0110792 A9 | 5/2007 | Simon |
| 2007/0135528 A1 | 6/2007 | Butler et al. |
| 2007/0149435 A1 | 6/2007 | Koenig et al. |
| 2007/0225388 A1 | 9/2007 | Cooper et al. |
| 2007/0298064 A1 | 12/2007 | Koslow |
| 2008/0008906 A1 | 1/2008 | Catalfamo |
| 2008/0019935 A1 | 1/2008 | Khan |
| 2008/0035174 A1 | 2/2008 | Aubrun-sonneville |
| 2008/0083420 A1 | 4/2008 | Glenn et al. |
| 2008/0090939 A1 | 4/2008 | Netravali et al. |
| 2008/0131695 A1 | 6/2008 | Aouad et al. |
| 2008/0138492 A1 | 6/2008 | Cingotti |
| 2008/0149119 A1 | 6/2008 | Shen |
| 2008/0152894 A1 | 6/2008 | Beihoffer et al. |
| 2008/0153730 A1 | 6/2008 | Tsaur |
| 2008/0215023 A1 | 9/2008 | Scavone et al. |
| 2008/0269095 A1 | 10/2008 | Aubrun-Sonneville |
| 2008/0276178 A1 | 11/2008 | Fadell et al. |
| 2008/0292669 A1 | 11/2008 | Deng et al. |
| 2008/0293839 A1 | 11/2008 | Stobby |
| 2009/0004254 A1 | 1/2009 | Maibach |
| 2009/0041820 A1 | 2/2009 | Wu et al. |
| 2009/0061225 A1 | 3/2009 | Bailey et al. |
| 2009/0061496 A1 | 3/2009 | Kuhn |
| 2009/0061719 A1 | 3/2009 | Shibutani |
| 2009/0155326 A1 | 6/2009 | Mack |
| 2009/0181587 A1 | 7/2009 | Kang |
| 2009/0197787 A1 | 8/2009 | Venet et al. |
| 2009/0232873 A1 | 9/2009 | Glenn, Jr. et al. |
| 2009/0249558 A1 | 10/2009 | Fileccia |
| 2009/0258099 A1 | 10/2009 | Brown et al. |
| 2009/0263342 A1 | 10/2009 | Glenn, Jr. et al. |
| 2009/0285718 A1 | 11/2009 | Privitera |
| 2009/0291282 A1 | 11/2009 | Kitamura et al. |
| 2010/0018641 A1 | 1/2010 | Branham |
| 2010/0021517 A1 | 1/2010 | Ahlers |
| 2010/0098745 A1 | 4/2010 | Staab |
| 2010/0105821 A1 | 4/2010 | Verrall |
| 2010/0135921 A1 | 6/2010 | Hughes et al. |
| 2010/0150976 A1 | 6/2010 | Schnitzler |
| 2010/0166854 A1 | 7/2010 | Michniak-Kohn |
| 2010/0167971 A1 | 7/2010 | Glenn, Jr. et al. |
| 2010/0173817 A1 | 7/2010 | Glenn, Jr. et al. |
| 2010/0179083 A1 | 7/2010 | Glenn, Jr. et al. |
| 2010/0196440 A1 | 8/2010 | Stark |
| 2010/0266668 A1 | 10/2010 | Coffee |
| 2010/0279905 A1 | 11/2010 | Glenn, Jr. |
| 2010/0285101 A1 | 11/2010 | Moore |
| 2010/0286011 A1 | 11/2010 | Glenn, Jr. et al. |
| 2010/0291165 A1 | 11/2010 | Glenn, Jr. et al. |
| 2010/0298188 A1 | 11/2010 | Glenn, Jr. et al. |
| 2011/0014252 A1 | 1/2011 | Sagel et al. |
| 2011/0023240 A1 | 2/2011 | Fossum |
| 2011/0027328 A1 | 2/2011 | Baig et al. |
| 2011/0028373 A1 | 2/2011 | Fossum et al. |
| 2011/0028374 A1 | 2/2011 | Fossum et al. |
| 2011/0033509 A1 | 2/2011 | Simon |
| 2011/0136719 A1 | 6/2011 | Jalbert |
| 2011/0159267 A1 | 6/2011 | Lee |
| 2011/0165110 A1 | 7/2011 | Kinoshita et al. |
| 2011/0182956 A1 | 7/2011 | Glenn, Jr. et al. |
| 2011/0189246 A1 | 8/2011 | Glenn, Jr. et al. |
| 2011/0189247 A1 | 8/2011 | Glenn, Jr. |
| 2011/0195098 A1 | 8/2011 | Glenn, Jr. et al. |
| 2011/0223381 A1 | 9/2011 | Sauter |
| 2011/0230112 A1 | 9/2011 | Rose |
| 2011/0250256 A1 | 10/2011 | Hyun-oh et al. |
| 2011/0287687 A1 | 11/2011 | Kramer et al. |
| 2011/0301070 A1 | 12/2011 | Ochomogo |
| 2012/0021026 A1 | 1/2012 | Glenn, Jr. |
| 2012/0027838 A1 | 2/2012 | Gordon et al. |
| 2012/0048769 A1 | 3/2012 | Sivik |
| 2012/0052036 A1 | 3/2012 | Glenn, Jr. |
| 2012/0052037 A1 | 3/2012 | Sivik et al. |
| 2012/0053103 A1 | 3/2012 | Sivik |
| 2012/0053108 A1 | 3/2012 | Glenn, Jr. |
| 2012/0058100 A1 | 3/2012 | Shastri et al. |
| 2012/0058166 A1 | 3/2012 | Glenn, Jr. |
| 2012/0082037 A1 | 4/2012 | Wang |
| 2012/0107534 A1 | 5/2012 | Wnuk et al. |
| 2012/0172831 A1 | 7/2012 | Darcy |
| 2012/0215148 A1 | 8/2012 | Ewert |
| 2012/0237576 A1 | 9/2012 | Gordon |
| 2012/0258902 A1 | 10/2012 | Parrish et al. |
| 2012/0270029 A1 | 10/2012 | Glenn, Jr. et al. |
| 2012/0288693 A1 | 11/2012 | Stanley et al. |
| 2012/0294823 A1 | 11/2012 | Aramwit |
| 2012/0321580 A1 | 12/2012 | Glenn, Jr. |
| 2013/0236520 A1 | 9/2013 | Popovsky et al. |

(56) References Cited

U.S. PATENT DOCUMENTS

| | | |
|---|---|---|
| 2013/0303419 A1 | 11/2013 | Glenn, Jr. et al. |
| 2014/0105946 A1 | 4/2014 | Glenn, Jr. et al. |
| 2014/0127145 A1 | 5/2014 | Deckner |
| 2014/0271744 A1 | 9/2014 | Glenn, Jr. et al. |
| 2014/0329428 A1 | 11/2014 | Glenn, Jr. |
| 2015/0044157 A1 | 2/2015 | Kulkarni et al. |
| 2015/0102307 A1 | 4/2015 | Tajima et al. |
| 2015/0297494 A1 | 10/2015 | Mao |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |
| 2016/0008235 A1 | 1/2016 | Sivik et al. |
| 2016/0101026 A1 | 4/2016 | Pratt |
| 2016/0101204 A1 | 4/2016 | Lynch et al. |
| 2016/0143827 A1 | 5/2016 | Castan Barberan et al. |
| 2016/0250109 A1 | 9/2016 | Dreher et al. |
| 2016/0324741 A1 | 11/2016 | Baig |
| 2016/0367104 A1 | 12/2016 | Dreher et al. |
| 2017/0121641 A1 | 5/2017 | Smith |
| 2017/0335080 A1 | 11/2017 | Mao et al. |
| 2018/0015643 A1 | 1/2018 | Patel et al. |
| 2018/0110710 A1 | 4/2018 | Zhao et al. |
| 2018/0140469 A1 | 5/2018 | Kane et al. |
| 2018/0163325 A1 | 6/2018 | Glenn, Jr. et al. |
| 2018/0258555 A1 | 9/2018 | Glenn, Jr. |
| 2018/0311135 A1 | 11/2018 | Chang et al. |
| 2018/0333339 A1 | 11/2018 | Hamersky |
| 2018/0334644 A1 | 11/2018 | Hamersky et al. |
| 2019/0015875 A1 | 1/2019 | Gardner, Jr. et al. |
| 2019/0282457 A1 | 9/2019 | Pratt |
| 2019/0282461 A1 | 9/2019 | Glassmeyer |
| 2019/0350819 A1 | 11/2019 | Hamersky et al. |
| 2020/0071851 A1 | 3/2020 | Glenn, Jr. et al. |
| 2020/0214946 A1 | 7/2020 | Chan et al. |
| 2020/0261326 A1 | 8/2020 | Sivik et al. |
| 2020/0275818 A1 | 9/2020 | Dreher et al. |
| 2020/0308360 A1 | 10/2020 | Mao et al. |
| 2020/0405587 A1 | 12/2020 | Song |
| 2021/0000733 A1 | 1/2021 | Hilvert |
| 2021/0094744 A1 | 4/2021 | Benson et al. |
| 2021/0107263 A1 | 4/2021 | Bartolucci et al. |
| 2021/0128417 A1 | 5/2021 | Sivik et al. |
| 2021/0137798 A1 | 5/2021 | Sivik et al. |
| 2021/0147763 A1 | 5/2021 | Tan et al. |
| 2021/0189602 A1 | 6/2021 | Glenn, Jr. et al. |
| 2021/0401677 A1 | 12/2021 | Song |
| 2022/0257476 A1 | 8/2022 | Hamersky et al. |
| 2022/0323309 A1 | 10/2022 | Pratt et al. |

FOREIGN PATENT DOCUMENTS

| | | |
|---|---|---|
| CA | 2695068 A1 | 9/2010 |
| CA | 166297 | 5/2018 |
| CA | 169627 S | 5/2018 |
| CN | 1138091 | 12/1996 |
| CN | 1219388 | 6/1999 |
| CN | 1268558 | 10/2000 |
| CN | 1357613 A | 7/2002 |
| CN | 1454231 A | 11/2003 |
| CN | 1473194 A | 2/2004 |
| CN | 1530431 A | 9/2004 |
| CN | 1583991 A | 2/2005 |
| CN | 1726074 A | 1/2006 |
| CN | 3648760 | 5/2007 |
| CN | 101161877 A | 4/2008 |
| CN | 102006852 A | 4/2011 |
| CN | 301666535 | 9/2011 |
| CN | 102647973 A | 8/2012 |
| CN | 103282015 A | 9/2013 |
| CN | 103735428 A | 4/2014 |
| CN | 104040061 A | 9/2014 |
| CN | 304115833 | 4/2017 |
| CN | 106726634 A | 5/2017 |
| CN | 106728634 A | 5/2017 |
| CN | 304537587 | 3/2018 |
| CN | 109589279 B | 3/2020 |
| DE | 19607851 A1 | 9/1997 |
| DE | 10331767 A1 | 2/2005 |
| EP | 0392608 A2 | 10/1990 |
| EP | 609808 A1 | 8/1994 |
| EP | 0858828 A1 | 8/1998 |
| EP | 0948960 A2 | 10/1999 |
| EP | 1214879 A2 | 6/2002 |
| EP | 1227152 A1 | 7/2002 |
| EP | 1217987 B1 | 12/2004 |
| EP | 1574561 A1 | 9/2005 |
| EP | 1160311 B1 | 3/2006 |
| EP | 1887036 A2 | 2/2008 |
| EP | 1958532 A2 | 8/2008 |
| EP | 2085434 A1 | 8/2009 |
| EP | 1317916 B1 | 10/2010 |
| EP | 2246031 A1 | 11/2010 |
| FR | 2871685 A1 | 12/2005 |
| FR | 2886845 A1 | 12/2006 |
| GB | 2107579 A | 5/1983 |
| GB | 2235204 A | 2/1991 |
| GB | 2355008 A | 4/2001 |
| GB | 2378407 A | 2/2003 |
| JP | S4912158 A | 2/1974 |
| JP | 58021608 | 2/1983 |
| JP | S58216109 A | 12/1983 |
| JP | S59163458 A | 9/1984 |
| JP | S6272609 A | 4/1987 |
| JP | S6272610 A | 4/1987 |
| JP | S6281432 A | 4/1987 |
| JP | S6281462 A | 4/1987 |
| JP | H01172319 A | 12/1987 |
| JP | S6346251 A | 2/1988 |
| JP | S63156715 A | 6/1988 |
| JP | H01313418 A | 12/1989 |
| JP | H0275650 A | 3/1990 |
| JP | H05344873 A | 12/1993 |
| JP | H0617083 A | 1/1994 |
| JP | H06116598 A | 4/1994 |
| JP | 0753349 | 2/1995 |
| JP | H0789852 A | 4/1995 |
| JP | H08325133 A | 12/1996 |
| JP | H09216909 A | 8/1997 |
| JP | 10158700 A | 6/1998 |
| JP | H10251371 A | 9/1998 |
| JP | H11513053 A | 11/1999 |
| JP | 2000053998 A | 2/2000 |
| JP | 2000169896 A | 6/2000 |
| JP | 2000229841 A | 8/2000 |
| JP | 2001519376 A | 10/2001 |
| JP | 2001520983 A | 11/2001 |
| JP | 2002201531 A | 7/2002 |
| JP | 2002226895 A | 8/2002 |
| JP | 2003073700 A | 3/2003 |
| JP | 2003082397 A | 3/2003 |
| JP | 2004509198 A | 3/2004 |
| JP | 2004256799 A | 9/2004 |
| JP | 2004533551 A | 11/2004 |
| JP | 2004345983 A | 12/2004 |
| JP | 2005171063 A | 6/2005 |
| JP | 2005538202 A | 12/2005 |
| JP | 2006056835 A | 3/2006 |
| JP | 3828217 B2 | 7/2006 |
| JP | 2007001889 A | 1/2007 |
| JP | 2007091954 A | 4/2007 |
| JP | 2007197365 A | 8/2007 |
| JP | 2007197540 A | 8/2007 |
| JP | 2007528748 A | 10/2007 |
| JP | 2008156807 A | 7/2008 |
| JP | 2008525436 A | 7/2008 |
| JP | 2009079329 A | 4/2009 |
| JP | 2009533569 A | 9/2009 |
| JP | 2013505375 A | 2/2013 |
| JP | 2013531145 A | 8/2013 |

(56) References Cited

FOREIGN PATENT DOCUMENTS

| | | | |
|---|---|---|---|
| JP | 2013531748 A | 8/2013 |
| JP | 2015509147 A | 3/2015 |
| JP | 5821609 B2 | 10/2015 |
| JP | 6272610 B2 | 1/2018 |
| KR | 20020003442 A | 1/2002 |
| KR | 20040094520 A | 11/2004 |
| WO | 8301943 A1 | 6/1983 |
| WO | 9514495 A1 | 6/1995 |
| WO | 9951715 A1 | 10/1999 |
| WO | 9957155 A1 | 11/1999 |
| WO | 0042992 A2 | 7/2000 |
| WO | 0107194 A1 | 2/2001 |
| WO | 0119948 A1 | 3/2001 |
| WO | 0125322 A1 | 4/2001 |
| WO | 0125393 A1 | 4/2001 |
| WO | 200125322 A1 | 4/2001 |
| WO | 2001024770 A1 | 4/2001 |
| WO | 200154667 A1 | 8/2001 |
| WO | 2001054667 A1 | 8/2001 |
| WO | 0238722 A2 | 5/2002 |
| WO | 2004032859 A1 | 4/2004 |
| WO | 2004041991 A1 | 5/2004 |
| WO | 2005003423 A1 | 1/2005 |
| WO | 2005070374 A1 | 8/2005 |
| WO | 2005075547 A1 | 8/2005 |
| WO | 2006106514 A2 | 10/2006 |
| WO | 2006130647 A1 | 12/2006 |
| WO | 2007022229 A1 | 2/2007 |
| WO | 2007033598 A1 | 3/2007 |
| WO | 2007093558 A1 | 8/2007 |
| WO | 2007093619 A1 | 8/2007 |
| WO | 2007102119 A1 | 9/2007 |
| WO | 2008049242 A1 | 5/2008 |
| WO | 2008104954 A2 | 9/2008 |
| WO | 2009019571 A1 | 2/2009 |
| WO | 2009095891 A1 | 8/2009 |
| WO | 2010006708 A1 | 1/2010 |
| WO | 2010077627 A2 | 7/2010 |
| WO | 2010085569 A1 | 7/2010 |
| WO | 2012120199 A1 | 9/2012 |
| WO | DM100932 | 4/2018 |
| WO | DM100938 | 4/2018 |
| WO | DM101063 | 5/2018 |
| WO | DM101100 | 5/2018 |
| WO | DM101101 | 5/2018 |
| WO | 2019001940 A1 | 1/2019 |

OTHER PUBLICATIONS

All final and non-final office actions for U.S. Appl. No. 16/431,115.
All final and non-final Office Actions, U.S. Appl. No. 15/979,961.
All final and non-final Office Actions, U.S. Appl. No. 15/981,096.
PCT International Search Report and Written Opinion for PCT/US2018/015363 dated Jun. 4, 2018.
PCT International Search Report and Written Opinion for PCT/US2018/015364 dated Oct. 1, 2018.
PCT International Search Report and Written Opinion for PCT/US2018/030762 dated Aug. 7, 2018.
Adhesives Research (Pennsylvania, http://12.4.33.51/news/apresmed.htm).
All final and non-final office actions for U.S. Appl. No. 14/690,593.
All final and non-final office actions for U.S. Appl. No. 15/665,886.
All final and non-final office actions for U.S. Appl. No. 16/589,504.
All final and non-final office actions for U.S. Appl. No. 16/901,548.
All final and non-final office actions for U.S. Appl. No. 16/912,876.
All final and non-final office actions for U.S. Appl. No. 16/918,292.
All final and non-final office actions for U.S. Appl. No. 29/672,822.
All final and non-final office actions for U.S. Appl. No. 29/676,338.
All final and non-final office actions for U.S. Appl. No. 29/707,807.
All final and non-final office actions for U.S. Appl. No. 29/707,809.
All final and non-final office actions for U.S. Appl. No. 29/728,687.
All final and non-final office actions for U.S. Appl. No. 29/728,688.
All Office Actions, U.S. Appl. No. 16/953,975.
All Office Actions, U.S. Appl. No. 17/070,205.
All Office Actions, U.S. Appl. No. 29/766,885.
Amerilab Technologies, Inc. (Minnesota, http://www.amerilabtech.comm/).
Anonymous "P8136 Poly(vinyl alcohol)" Internet article, [Online] XP002538935 retrieved from the Internet: URL:hllp/20NWW.sigmaaldrich.com/catalog/ProductDetail.do?D7=0%N25-SEARCH_CONCAT PNOIBRAND KEY%N4=P8136%7SCIAL%N25=0%QS=ON%F=SPEC retrieved on Jul. 28, 2009.
Briscoe et al. "The effects of hydrogen bonding upon the viscosity of aqueous poly( vinyl alcohol) solutions," from Polymer, 41 (2000), pp. 3851-3860.
Cardinal Health (Dublin, Ohio, http://spd.cardinal.com/).
Cima Labs, Inc. (Minnesota, http://www.cimalabs.com/).
Design of "Detergent tablets" (Design Registration No. 000634142-0003), (No. of Publicly known information: HH18274488), Registered Community Designs Bulletin, published by EUIPO on Jan. 9, 2007.
Design of "Detergent tablets" (Design Registration No. 000634142-0004), (No. of Publicly known information: HH18274489), Registered Community Designs Bulletin, published by EUIPO on Jan. 9, 2007.
Design of "Soaps" accepted on Jul. 11, 1986, Publishing Office: Korean Intellectual Property Office (KIPO), Document Name: Design Gazette (Application No. 3019850005996), Publication Date: Jun. 9, 1986, (No. of Publicly known information: HG21900612).
Dissolving Soap Strips (Ranir LLC, Michigan, www.ranir.com).
Encyclopedia of Polymer Science and Engineering, vol. 15, 2nd ed., pp. 204 308 Silicones, 1989.
Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.
Hexagon 4 ward soap mold, Soap, Cosmetics, New Silicon mold, Published on Sep. 29, 2016, Retrieved from Internet: http://candlebox.com/product/%EC%9C%A1%EA%B0%81-4%EA%B5%AC-%EB%B9%84%EB%88%84%EB%AA%B0 %EB%93%9C/2206/?page_4=3#none.
Hildebrand, T., et al. "Quantification of bone microarchitecture with the structure mode index", Computer Methods in Biomechanics and Biomedical Engineering, vol. 1, Jan. 14, 1997, pp. 15-23.
How Gemz work?, Gemz Hair Care, published on Oct. 1, 2018, retrieved on Apr. 27, 2021, retrieved from the Internet URL: https://www.youtube.com/watch?v=ts1waYk43g4.
https://www.craftcuts.com/hexagon-craft-shape.htmlHexagon wood cutouts, www.craftcuts.com, 1 page, reviewed as early as May 2018 (Year: 2018).
Japanese Paper Soap (http://www.wishingfish.com/papersoap.html).
Kuraray: "Mowiol—Technical data sheet", Jun. 1, 2010 (Jun. 1, 2010),pp. 1-4, XP055119891, Retrieved from the Internet: URL:http://www.kuraray.eu/fileadmin/Downloads/mowiol/TDS_Mowiol_en_20110624.pdf [retrieved on May 23, 2014].
Le Laboratoire du Bain (France, http://www.laboudubain.com/).
M.K. Industries (Gujarat India, http://www.soapstrips.com).
Megulars Car Wash Strips: Megulars Inc. California, http://www.automotivedigesl.com/view_art.asp?articles!D=12414.
Michelle Villett, Why You Need a Sulfate-Free Shampoo, The Skincare Edit, updated date: Jan. 25, 2019, Original publication date: Feb. 22, 2016 (Year: 2016), 7 pages.
MOVA Pharmaceutical and Kosmos (USA, http:/lwww.icon-pr.com/news/news/prinl.cfm?inv_id=256-1).
Okasaka et al., "Evaluation of Anionic Surfactants Effects on the Skin Barrier Function Based on Skin Permeability", Pharmaceutical Development and Technology, vol. 24, No. 1, Jan. 23, 2018, pp. 99-104.
Product Review: Gemz Solid Shampoo, Travel as Much, published on Mar. 19, 2019, retrieved on Apr. 27, 2021, retrieved from the Internet URL: https://travelasmuch.com/gemz-solid-shampoo-review/.
Pure Soap Leafz: (Soap Unltd. Netherlands, http://www.upandunder.com.uk/eshop/catalogue/testbs.asp?Manufacturer_ID=252&Activity_ID=33&Description_ID=157).
Sanipro Sanitary Products (Italy, http://www.sanipro.iit).

(56) References Cited

OTHER PUBLICATIONS

Solublon (Toyohashi Japan, http://www.solublon.com).
SPI Pharma (Delaware, http://www.spipharma.com).
Travelers Passport Paper Soap Sheets (http://www.weddingflavornow.com/index.asp?PageAction=VIEWPROD&PROD&ProdID=510).
Vaughan, C.D. "Solubility, Effects in Product, Package, Penetration and Preservation", Cosmetics and Toiletries, vol. 103, Oct. 1988.
Veslerby, A.: "Star Volume in Bone Research: A Histomorphometric Analysis of Trabecular Bone Structure UsingVertical Sections", Anal Rec: Feb. 1993, 232(2), pp. 325-334.
Wenda (China, http://www.wenda.com).
Zhang et al. "Study on Morphology of Electrospun Poly( vinyl alcohol) Mats," European Polymer Journal 41 (2005), pp. 423-432.
U.S. Appl. No. 29/728,688, filed Mar. 20, 2020, Douglas Charles Cook et al.
U.S. Appl. No. 29/728,687, filed Mar. 20, 2020, Douglas Charles Cook et al.
U.S. Appl. No. 29/707,809, filed Oct. 1, 2019, Sharonda Lee Crawford Washington et al.
U.S. Appl. No. 29/707,807, filed Oct. 1, 2019, Sharonda Lee Crawford Washington et al.
U.S. Appl. No. 29/766,885, filed Jan. 19, 2021, Wee Hau Tan et al.
All Office Actions; U.S. Appl. No. 17/357,119, filed Jun. 24, 2021.
All Office Actions: U.S. Appl. No. 29/815,500, fifed Nov. 15, 2021.
Definition of Derivative by Merriam Webster Online Dictionary, Year, 2021.
Raymond C Rowe et al., Polyvinyl Alcohol, Handbook of Pharmaceutical Excipients, 2009, Sixth Edition, Pharmaceutical Press, 564-565.
Sahin et al. "A Study on Physical and Chemical Properties of Cellulose Paper Immersed in Various Solvent Mixtures" International Journal of Molecular Sciences, Jan. 2008; 9(1): 78-88.
Wermuth et al. Drug Discovery, "Drug Discovery Today, 2006", vol. 11 7/8, 348-354, Year 2006.
Dow, UCARE™ Polymer LR-400, Technical Data Sheet, Downloaded in Mar. 2022, 4 pages.
Karen Duis et al, "Environmental fate and effects of water-soluble synthetic organic polymers used in cosmetic products", Environmental Sciences Europe, vol. 33, Article No. 21, Feb. 16, 2021, 78 pages.
All Office Actions; U.S. Appl. No. 29/819,499, filed Dec. 15, 2021.
Color Keeper [online], [site visited Oct. 18, 2021]. Available from internet, URL: https://shopgemz.com/products/color-keeper?variant=13094595002434&utm_source=google&utm_medium=cpc&utm_campaign=Shopping&gclid=Cj0KCQjw5JSLBhCxARIsAHgO2SdAT7LTehpyxM1qTGtnFETDaINuo9_cQSO pPwCmsmmd-GA1Y0USekQEaAh0iEALw_wcB (Year: 2021).
Gemz Hair Care. Perfect Pairs. Publication date unavailable. Visited Jan. 26, 2022. https://shopgemz.com/collections/perfect-pairs (Year: 0).
Paper Pieces Hexagons, announced 2018 [online], [site visited Oct. 14, 2021]. Available from internet, URL:https://www.amazon.com/Paper-Pieces-HEX100B-Hexagons-1200pc/dp/B07DVYV2HN/ (Year: 2018).
Rounded hexagon shape, announced 2016 [online], [site visited Oct. 20, 2021], Available from internet, URL:https://www.vexels.com/png-svg/preview/139199/rounded-hexagon-shape (Year: 2016).
"Green Chemistry", Huazhong University of Science and Technology Press, published on Jun. 30, 2008, pp. 6.
Ni Genshan et al. "Drug Classification and Pharmacology Summary", PLA Press, published on Apr. 30, 1988, pp. 3.
Hiroshi Yagi & 4 Others, Research Study of a Friction Protector for Preventing a Tow Line From Breaking,Working Papers for Fiscal 2006 I Japan I Japan Coast Guard Dec. 2007, pp. 1-8.
Latorre Carmen, Nanotribological Effects of Hair Careproducts and Environment on Human Hair Using Atomic Forcemicroscopy,Journal of Vacuum Science and Technology Part A, U.S.A, AVS/AIP , Jun. 28, 2005 , V2 3 N 4, p. 1034-1045.
Afifi-Effat et al., Polymer Letters, 9: 651-655 (1971).
All Office Actions; U.S. Appl. No. 13/173,639, filed Jun. 30, 2011.
All Office Actions; U.S. Appl. No. 13/229,825, filed Sep. 12, 2011.
All Office Actions; U.S. Appl. No. 14/334,862, filed Jul. 18, 2014.
All Office Actions; U.S. Appl. No. 15/170,125, filed Jun. 1, 2016.
All Office Actions; U.S. Appl. No. 15/374,486, filed Dec. 9, 2016.
All Office Actions; U.S. Appl. No. 15/978,503, filed May 14, 2018.
All Office Actions; U.S. Appl. No. 16/674,837, filed Nov. 5, 2019.
All Office Actions; U.S. Appl. No. 17/184,712, filed Feb. 25, 2021.
All Office Actions; U.S. Appl. No. 17/730,390, filed Apr. 27, 2022.
Ashland, KLUCEL hydroxypropylcelllose, accessed at http://www.ashland.com/Ashland/Static/Documents/ASI/PC_11229_Klucel_HPC.pdf on Apr. 20, 2016.
Francis Ignatious, Linghong Sun, Chao-Pin Lee, and John Baldoni. Electrospun Nanofibers in Oral Drug Delivery—ExpertReview. Pharmaceutical Research, vol. 27, No. 4, Apr. 2010, pp. 576-588. Published online Feb. 9, 2010.
Makadia, et al., "Poly Lactic-co-Glycolic Acid (PLGA) as Biodegradable Controlled Drug Delivery Carrier", Polymers, 3, pp. 1377-1397 (2011).
Ménard et al., "Gnotobiotic Mouse Immune Response Induced by *Bifidobacterium* sp. Strains Isolated from Infants", Applied and Environmental Microbiology, vol. 74, Issue 3, Feb. 1, 2008, pp. 660-666.
Minifibers, Inc., accessed on line at http://www.minifibers.com/documents/Choosing-the-Proper-Short-Cut-Fiber.pdf Oct. 3, 2016.
Overview of pharmaceutical excipients used in tablets and capsules in Drug Topics, dated Oct. 24, 2008. Downloaded Sep. 20, 2016 from http://drugtopics.modernmedicine.com/drugtopics/news/modernmedicine/modernmedicinenews/overviewpharmaceuticalexcipientsusedtablets.
Smith, et al., "Nanofibrous Scaffolds and Their Biological Effects", Nanotechnologies for the Life Sciences, vol. 9, pp. 188-215 (2006).
W S Ratnayake and D S Jackson. Gelatinization and solubility of corn starch during heating in excess water. Faculty u Publications in Food Science and Technology, Jan. 1, 2006. Also published in Journal of Agricultural and Food Chemistry 54:1 O(2006), pp. 3712-3716.
Yasuhiro Hiramatsu et al. "Bifidobacterium Components Have Immunomodulatory Characteristics Dependent on the Method of Preparation" Cytotechnology, Kluwer Academic Publishers, Do, vol. 55, Issue Nos. 2-3, Nov. 1, 2007, pp. 79-87.

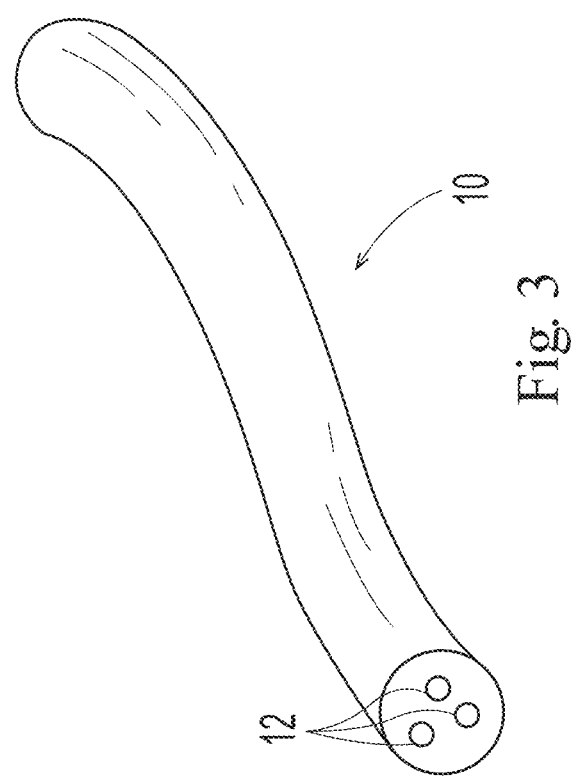

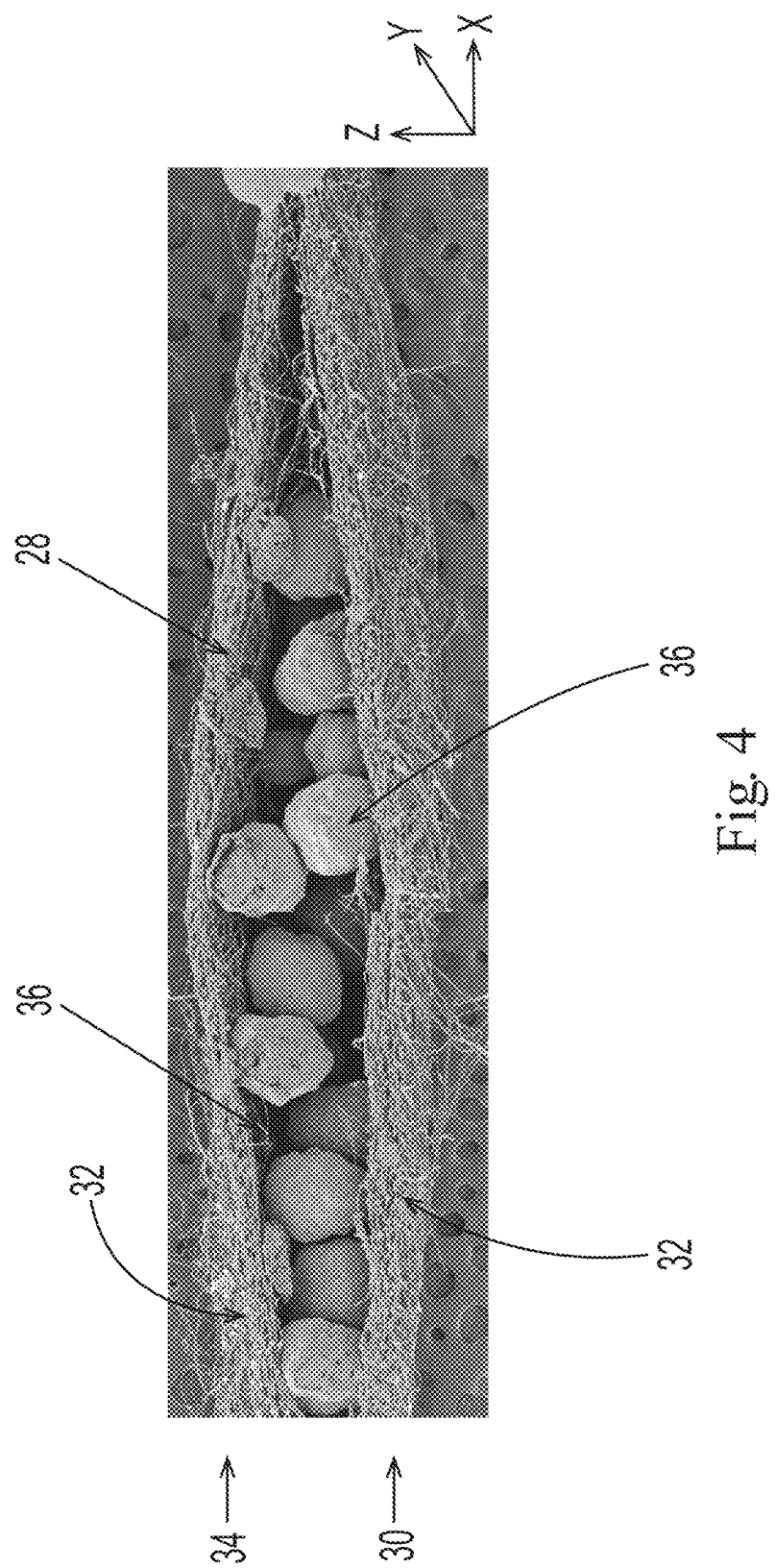

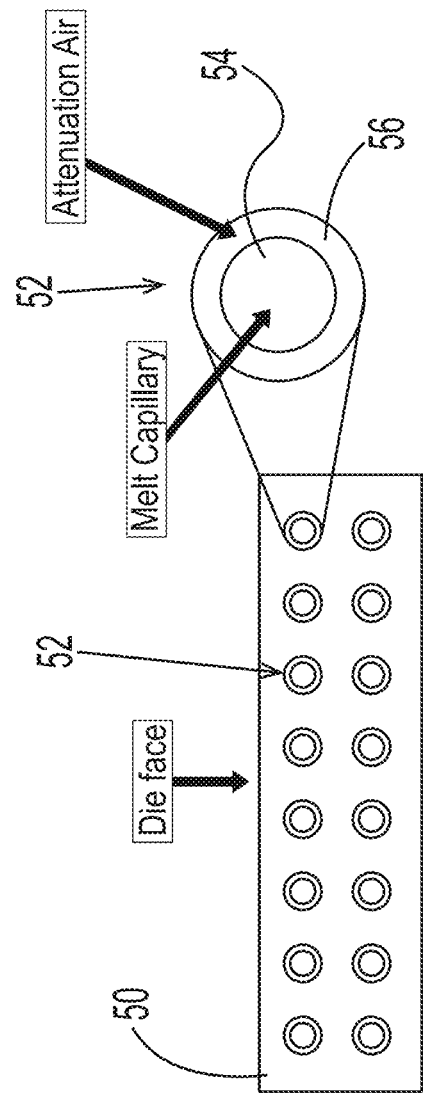

FIBROUS STRUCTURES CONTAINING POLYMER MATRIX PARTICLES WITH PERFUME INGREDIENTS

FIELD OF THE INVENTION

The present invention relates to fibrous structures, more particularly to fibrous structures comprising one or more polymer matrix particles that contain hydrophobic benefit agents including perfume ingredients.

BACKGROUND OF THE INVENTION

Many personal care and other consumer products, including conditioners, in the market today are sold in liquid form. While widely used, liquid products often have tradeoffs in terms of packaging, storage, transportation, and convenience of use. Liquid consumer products typically are sold in bottles, which add cost as well as packaging waste, much of which ends up in land-fills.

It can be desirable to formulate conditioners as solid structures that can include dissolvable films, compressed powders in a solid, fibrous structures, porous foams, soluble deformable solids, powders, bars or prills. However, many of these executions are not ideal for consumers. For example, some products including many bars or prills, do not hydrate fast enough when exposed to water to satisfy the consumer's desire to quickly apply to the hair a liquid conditioner without undue effort to dissolve the product. And other products do not deliver the desirable amount of wet and/or dry conditioning, fragrance, and other benefits.

It has been found that the addition of perfumes and other hydrophobic benefit agents (either neat or encapsulated) in the solid structures can prevent the rapid and easy dissolution of the solid structure in water during use, which significantly reduces the consumer experience and product performance.

As such, there remains a need for a convenient fibrous structure that can be readily dispersed in water and contains hydrophobic benefit agents, including perfumes.

SUMMARY OF THE INVENTION

The fibrous structure with a plurality of fibrous elements comprising: (i) a polymeric structurant having a weight average molecular weight of from about 10,000 to about 6,000,000 g/mol; (ii) a high melting point fatty material having a carbon chain length C12-C22 or mixtures thereof, wherein the melting point is above 25° C.; and (iii) a cationic surfactant; wherein the polymeric structurant has a weight average molecular weight of from about 10,000 to about 6,000,000 g/mol. The fibrous structure can also contain agglomerated particles comprising one or more perfume matrix particles comprising: (i) from about 10% to about 70%, by weight of the matrix particle, perfume; (ii) from about 30% to about 90%, by weight of the matrix particle, matrix material selected from the group consisting of water-soluble polymers, polyvinyl alcohol, polysaccharides, cross-linking agents, catalysts, polyethylene glycols (PEG), starches, gums, gelatin, dextrins, as well as hydrolyzed gums and hydrolyzed gelatin, and combinations thereof; wherein the one or more perfume matrix particles have a leakage of less than 5% according to the Analysis of Free Perfume in Perfume Particles; wherein the agglomerated matrix particles are from about 200 microns to about 1000 microns according to the Median Particle Size Test Method described herein.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 3 is a schematic representation of an example of a fibrous element according to the present invention;

FIG. 4 is a scanning electron microscope photograph of a cross-sectional view of an example of a fibrous structure according to the present invention;

FIG. 9 is a schematic representation of an example of a die with a magnified view used in the process of FIG. 8;

DETAILED DESCRIPTION OF THE INVENTION

Figure 1B:
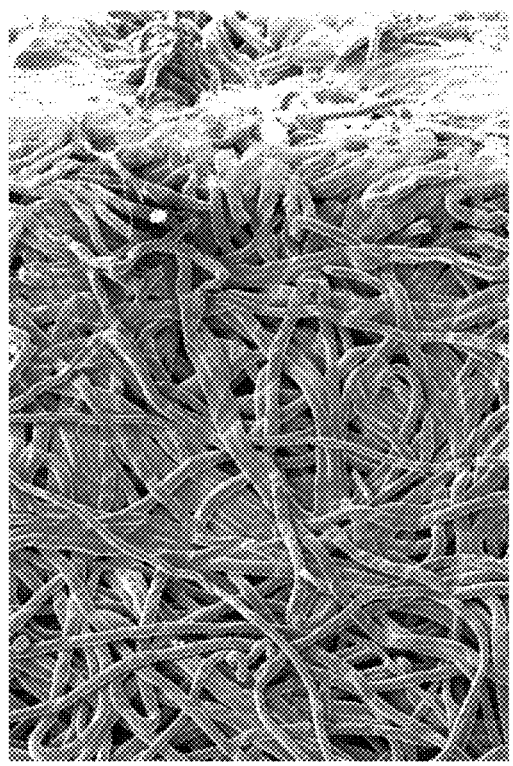
FIG. 1B is an example of a fibrous structure under 150× magnification where the filaments are clearly present.
Figure 1A:
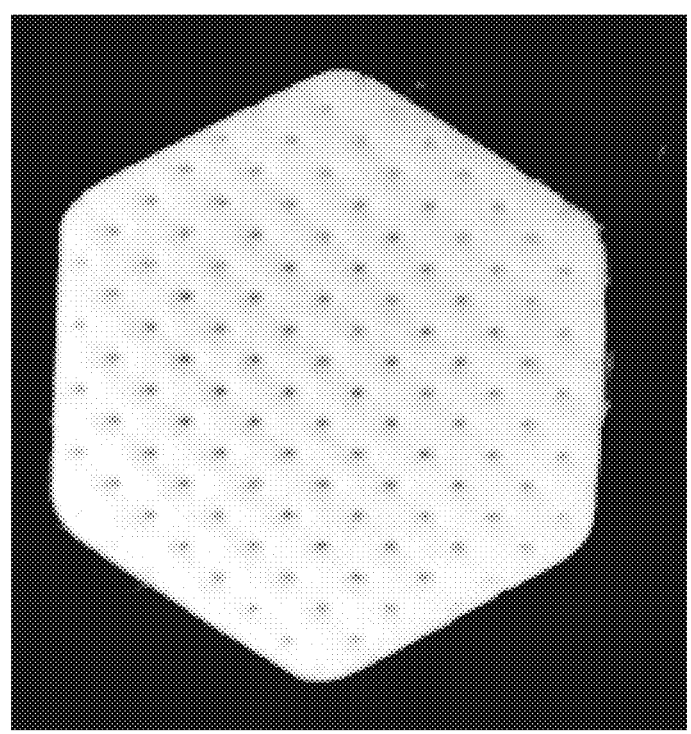
FIG. 1A is an example of a fibrous structure containing filaments.
Figure 1D:
FIG. 1D is an example of a fibrous structure after water is applied and shows how the cream spreads across a user's hands for application to the hair.
Figure 1C:
FIG. 1C is an example of a fibrous structure after water is applied and it becomes a fully homogenous cream.

It can be desirable for conditioners to be articles containing fibrous structures containing filaments that upon adding water rapidly forms a solution or dispersion that can be easily applied to a user's hair. FIG. 1A is an example of a fibrous structure containing filaments. FIG. 1B shows the multitude of discrete filaments under 150× magnification in a fibrous structure. FIGS. 1C and 1D shows the fibrous structure shortly after water is applied and the fibrous structure forms a fully homogenous cream. This cream is easy to apply to spread across the hair and provides uniform performance, including uniform conditioning.

However, it has been found that the addition of perfumes and other hydrophobic benefit agents (either neat or encapsulated) in or on the surface of the solid structures containing hair conditioner actives, can prevent the rapid and easy dissolution of the solid structure in water during use, which significantly reduces the consumer experience and product performance. It has been found that hydrophobic benefit agents, like perfumes, even when encapsulated, can leak and cause waxy structures in or on the surface of the dissolvable article.

While not willing to be bound by theory, it is believed that the leakage initially happens at the fiber level and then spreads over time, so when the consumer goes to use the article, the waxy structures inhibit the dissolution. For example, when the perfume ingredients come into contact with conditioner ingredients, such as the fatty alcohols, they can cause the ingredients to dissolve.

Figure 2A:
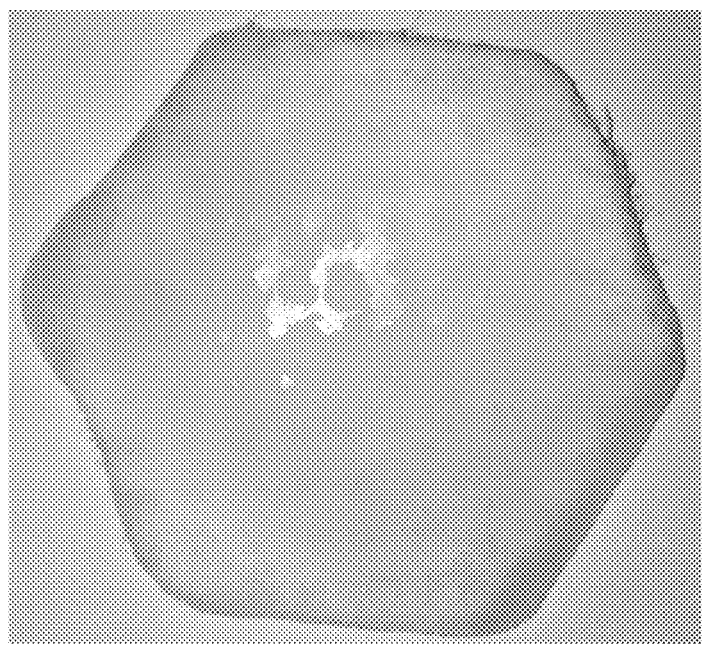
FIG. 2A is an example of a fibrous structure containing filaments with waxy structures.
Figure 2D:
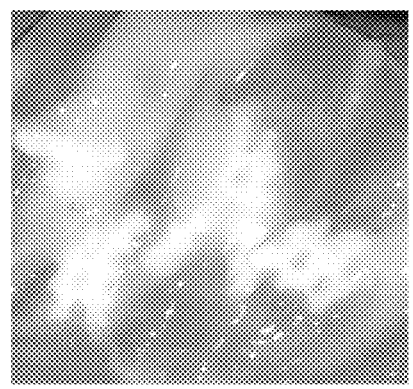
FIGS. 2C and 2D are example of a fibrous structure containing waxy structures after water is applied.
Figure 2C:
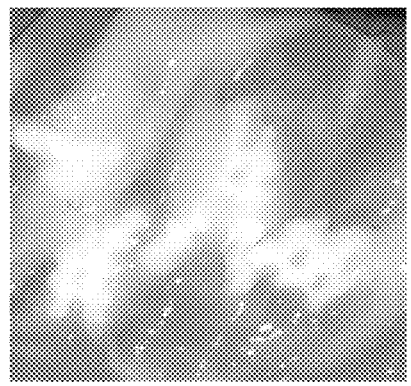
Figure 2B:
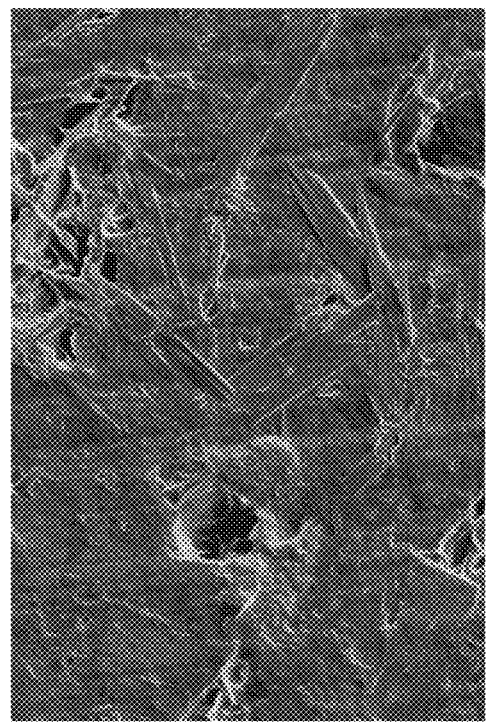
FIG. 2B is an example of a fibrous structure with waxy structures under 1131× magnification.

FIG. 2A is a photograph of a dissolvable structure with waxy structures. In FIG. 2A, the dissolvable structure had silicone and perfume sprayed on a surface of the web, which was in the middle of the structure. In FIG. 2A, the waxy structures are across most of the structure, even obscuring the perforations. FIG. 2B shows a fibrous structure, similar to the structure in FIG. 2A, with waxy structures under 1131× magnification. Even though the fibrous structure was formed with a multitude of filaments, in FIG. 2B, it is almost impossible to see the individual fibers, and the fibrous structure looks similar to a film, since the fibers appear fused together. Critically, when waxy structures are present, when water is applied to the fibrous structure, the structure does not rapidly form a uniform cream. Instead, as seen in FIGS. 2C and 2D, instead of a uniform, creamy foam, there are waxy bits that are not dispersed.

It has been found that adding matrix particles containing hydrophobic benefit agents, including perfumes, can have a leakage of less than 10%, alternatively less than 5%. The particle can be water-insoluble and/or anhydrous. In one example, the particle can contain from about 10-70 wt. % of a hydrophobic benefit agent, like perfume, and about 30 wt % to about 90 wt % matrix material, such as polysaccharide. In some examples, the matrix particle can further contain from one or more crosslinking agents. In another example, the matrix particle can be substantially free of or free of a crosslinking agent.

The fibrous structure can have an average hand dissolution score (initially and/or after one week at 40° C.) of less than or equal to 15, alternatively less than or equal to 13, alternatively less than or equal to 12, alternatively less than or equal to 10. The average hand dissolution score can be determined using the Hand Dissolution Method, described herein.

The fibrous elements can be substantially free of and/or free of perfumes. The fibrous elements can contain less than 1 wt %, less than 0.5 wt %, less than 0.1 wt %, and/or less than 0.05 wt % perfume.

Definitions

"Dissolvable" means that the Dissolvable Solid Structure is completely soluble in water or it provides a uniform dispersion upon mixing in water according to the Hand Dissolution Test, described hereafter.

"Fibrous structure" as used herein means a structure that comprises one or more fibrous elements and one or more particles. In one example, a fibrous structure according to the present invention means an association of fibrous elements and particles that together form a structure, such as a unitary structure, capable of performing a function.

The fibrous structures of the present invention may be homogeneous or may be layered. If layered, the fibrous structures may comprise at least two and/or at least three and/or at least four and/or at least five layers, for example one or more fibrous element layers, one or more particle layers and/or one or more fibrous element/particle mixture layer.

In one example, the fibrous structure can be a multi-ply fibrous structure that exhibits a basis weight of less than 5000 g/m2 as measured according to the Basis Weight Test Method described herein.

In one example, the fibrous structure of the present invention can be a "unitary fibrous structure."

"Unitary fibrous structure" as used herein is an arrangement comprising a one or more particles and a plurality of two or more and/or three or more fibrous elements that are inter-entangled or otherwise associated with one another to form a fibrous structure. A unitary fibrous structure of the present invention may be one or more plies within a multi-ply fibrous structure. In one example, a unitary fibrous structure of the present invention may comprise three or more different fibrous elements. In another example, a unitary fibrous structure of the present invention may comprise two different fibrous elements, for example a co-formed fibrous structure, upon which a different fibrous element is deposited to form a fibrous structure comprising three or more different fibrous elements.

"Fibrous element" as used herein means an elongate particulate having a length greatly exceeding its average diameter, i.e. a length to average diameter ratio of at least about 10. A fibrous element may be a filament or a fiber. In one example, the fibrous element can be a single fibrous element rather than a yarn comprising a plurality of fibrous elements.

The fibrous elements of the present invention may be spun from a filament-forming composition also referred to as fibrous element-forming compositions via suitable spinning process operations, such as meltblowing, spunbonding, electro-spinning, and/or rotary spinning.

The fibrous elements of the present invention may be monocomponent and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyester-amide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow of the present invention and then cutting the filament or filament tow into segments of less than 5.08 cm (2 in.) thus producing fibers.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more polymeric structurants and one or more other ingredients, such as surfactants and high melting point fatty compounds. Therefore, references to filament and/or filaments of the present invention herein also include fibers made from such filament and/or filaments unless otherwise noted. Fibers are typically considered discontinuous in nature relative to filaments, which are considered continuous in nature.

"Filament-forming composition" and/or "fibrous element-forming composition" as used herein means a composition that can be suitable for making a fibrous element of the present invention such as by meltblowing and/or spunbonding. The filament-forming composition comprises one or more polymeric structurants that exhibit properties that make them suitable for spinning into a fibrous element. In addition, the filament-forming composition may comprise one or more polar solvents, such as water, into which one or more, for example all, of the polymeric structurant and/or one or more, for example all, of surfactants are dissolved and/or dispersed prior to spinning a fibrous element, such as a filament from the filament-forming composition.

In one example as shown in FIG. 3, a filament 10 of the present invention made from a filament-forming composition of the present invention is such that one or more additives 12, for example one or more active agents, may be present in the filament rather than on the filament, such as a coating composition comprising one or more active agents, which may be the same or different from the active agents in the fibrous elements and/or particles.

In one example, one or more additives, such as active agents, may be present in the fibrous element and one or more additional additives, such as active agents, may be present on a surface of the fibrous element. In another example, a fibrous element of the present invention may comprise one or more additives, such as active agents, that are present in the fibrous element when originally made, but then bloom to a surface of the fibrous element prior to and/or when exposed to conditions of intended use of the fibrous element.

As used herein, "vinyl pyrrolidone copolymer" (and "copolymer" when used in reference thereto) refers to a polymer of the following structure (I):

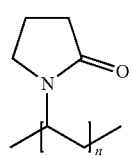

In structure (I), n is an integer such that the polymeric structurant has the degree of polymerization such that it possesses characteristics described herein. For purposes of clarity, the use of the term "copolymer" is intended to convey that the vinyl pyrrolidone monomer can be copolymerized with other non-limiting monomers such as vinyl acetate, alkylated vinyl pyrrolidone, vinyl caprolactam, vinyl valerolactam, vinyl imidazole, acrylic acid, methacrylate, acrylamide, methacrylamide, dimethacrylamide, alkylaminomethacrylate, and alkylaminomethacrylamide monomers.

As used herein, "vinyl acetate-vinyl alcohol copolymer" (and "copolymer" when used in reference thereto) refers to a polymer of the following structure (I):

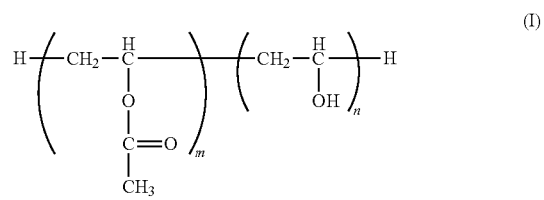

In structure (I), m and n are integers such that the polymeric structurant has the degree of polymerization and percent alcohol characteristics described herein. For purposes of clarity, this use of the term "copolymer" is intended to convey that the partially hydrolyzed polyvinyl acetate of the present invention comprises vinyl alcohol and vinyl acetate units. As discussed below, the polymeric structurant is routinely prepared by polymerizing vinyl acetate monomer followed by hydrolysis of some of the acetate groups to alcohol groups, as opposed to polymerization of vinyl acetate and vinyl alcohol monomer units (due in-part to the instability of vinyl alcohol).

"Particle" as used herein means a solid additive, such as a powder, granule, encapsulate, microcapsule, and/or prill. In one example, the particle exhibits a median particle size of 1600 μm or less as measured according to the Median Particle Size Test Method described herein. In another example, the particle exhibits a median particle size of from about 1 μm to about 1600 μm and/or from about 1 μm to about 800 μm and/or from about 5 μm to about 500 μm and/or from about 10 μm to about 300 μm and/or from about 10 μm to about 100 μm and/or from about 10 μm to about 50 μm and/or from about 10 μm to about 30 μm as measured according to the Median Particle Size Test Method described herein. The shape of the particle can be in the form of spheres, rods, plates, tubes, squares, rectangles, discs, stars, fibers or have regular or irregular random forms.

"Active agent-containing particle" as used herein means a solid additive comprising one or more active agents. In one example, the active agent-containing particle can be an active agent in the form of a particle (in other words, the particle comprises 100% active agent(s)). The active agent-containing particle may exhibit a median particle size of 1600 μm or less as measured according to the Median Particle Size Test Method described herein. In another example, the active agent-containing particle exhibits a median particle size of from about 1 μm to about 1600 μm and/or from about 1 μm to about 800 μm and/or from about 5 μm to about 500 μm and/or from about 10 μm to about 300 μm and/or from about 10 μm to about 100 μm and/or from about 10 μm to about 50 μm and/or from about 10 μm to about 30 μm as measured according to the Median Particle Size Test Method described herein. In one example, one or more of the active agents can be in the form of a particle that exhibits a median particle size of 20 μm or less as measured according to the Median Particle Size Test Method described herein.

In one example of the present invention, the fibrous structure comprises a plurality of particles, for example active agent-containing particles, and a plurality of fibrous elements in a weight ratio of particles, for example active agent-containing particles, to fibrous elements of 1:100 or greater and/or 1:50 or greater and/or 1:10 or greater and/or 1:3 or greater and/or 1:2 or greater and/or 1:1 or greater and/or from about 7:1 to about 1:100 and/or from about 7:1 to about 1:50 and/or from about 7:1 to about 1:10 and/or from about 7:1 to about 1:3 and/or from about 6:1 to 1:2 and/or from about 5:1 to about 1:1 and/or from about 4:1 to about 1:1 and/or from about 3:1 to about 1.5:1.

In another example of the present invention, the fibrous structure comprises a plurality of particles, for example active agent-containing particles, and a plurality of fibrous elements in a weight ratio of particles, for example active agent-containing particles, to fibrous elements of from about 7:1 to about 1:1 and/or from about 7:1 to about 1.5:1 and/or from about 7:1 to about 3:1 and/or from about 6:1 to about 3:1.

In yet another example of the present invention, the fibrous structure comprises a plurality of particles, for example active agent-containing particles, and a plurality of fibrous elements in a weight ratio of particles, for example active agent-containing particles, to fibrous elements of from about 1:1 to about 1:100 and/or from about 1:2 to about 1:50 and/or from about 1:3 to about 1:50 and/or from about 1:3 to about 1:10.

In another example, the fibrous structure of the present invention comprises a plurality of particles, for example active agent-containing particles, at a basis weight of greater than 1 g/m2 and/or greater than 10 g/m2 and/or greater than 20 g/m2 and/or greater than 30 g/m2 and/or greater than 40 g/m2 and/or from about 1 g/m2 to about 5000 g/m2 and/or to about 3500 g/m2 and/or to about 2000 g/m2 and/or from about 1 g/m2 to about 1000 g/m2 and/or from about 10 g/m2 to about 400 g/m2 and/or from about 20 g/m2 to about 300 g/m2 and/or from about 30 g/m2 to about 200 g/m2 and/or from about 40 g/m2 to about 100 g/m2 as measured by the Basis Weight Test Method described herein.

In another example, the fibrous structure of the present invention comprises a plurality of fibrous elements at a basis weight of greater than 1 g/m2 and/or greater than 10 g/m2 and/or greater than 20 g/m2 and/or greater than 30 g/m2 and/or greater than 40 g/m2 and/or from about 1 g/m2 to about 3000 g/m2 and/or from about 10 g/m2 to about 5000 g/m2 and/or to about 3000 g/m2 and/or to about 2000 g/m2 and/or from about 20 g/m2 to about 2000 g/m2 and/or from about 30 g/m2 to about 1000 g/m2 and/or from about 30 g/m2 to about 500 g/m2 and/or from about 30 g/m2 to about 300 g/m2 and/or from about 40 g/m2 to about 100 g/m2 and/or from about 40 g/m2 to about 80 g/m2 as measured by the Basis Weight Test Method described herein. In one example, the fibrous structure comprises two or more layers wherein fibrous elements are present in at least one of the layers at a basis weight of from about 1 g/m2 to about 300 g/m2.

"Conditions of intended use" as used herein means the temperature, physical, chemical, and/or mechanical conditions that a fibrous element and/or particle and/or fibrous structure of the present invention is exposed to when the fibrous element and/or particle and/or fibrous structure is used for one or more of its designed purposes. For instance, if a fibrous element and/or a particle and/or a fibrous structure comprising a fibrous element is designed to be used by a human as a shampoo for hair care purposes, the conditions of intended use will include those temperature, chemical, physical and/or mechanical conditions present during the shampooing of the human's hair. Likewise, if a fibrous element and/or a particle and/or a fibrous structure comprising a fibrous element is designed to be used in a dishwashing operation, by hand or by a dishwashing machine, the conditions of intended use will include the temperature, chemical, physical and/or mechanical conditions present in a dishwashing water and/or dishwashing machine, during the dishwashing operation.

"Active agent" as used herein means an additive that produces an intended effect in an environment external to a fibrous element and/or a particle and/or a fibrous structure comprising a fibrous element of the present invention, such as when the fibrous element and/or a particle and/or fibrous structure is exposed to conditions of intended use of the fibrous element and/or a particle and/or a fibrous structure comprising a fibrous element. In one example, an active agent comprises an additive that treats a surface, including a soft surface (i.e., hair, skin). In another example, an active agent comprises an additive that creates a chemical reaction (i.e., foaming, fizzing, coloring, warming, cooling, lathering, disinfecting and/or clarifying and/or chlorinating, such as in clarifying water and/or disinfecting water and/or chlorinating water). In yet another example, an active agent comprises an additive that treats an environment (i.e., deodorizes, purifies, perfumes). In one example, the active agent is formed in situ, such as during the formation of the fibrous element and/or particle containing the active agent, for example the fibrous element and/or particle may comprise a water-soluble polymer (e.g., starch) and/or a surfactant (e.g., anionic surfactant), which may create a polymer complex or coacervate that functions as the active agent used to treat the hair and/or scalp.

"Treats" as used herein with respect to treating a surface means that the active agent provides a benefit to a surface or environment. Treats includes regulating and/or immediately improving a surface's, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g., building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

"Weight ratio" as used herein means the ratio between two materials on their dry basis.

"Water-soluble material" as used herein means a material that is miscible in water. In other words, a material that is capable of forming a stable (does not separate for greater than 5 minutes after forming the homogeneous solution) homogeneous solution with water at ambient conditions.

"Water-insoluble" as used herein is meant that the material, particle, and/or substrate does not dissolve in or readily break apart upon immersion in water. In some instances, water-insoluble materials swell when exposed to water.

"Ambient conditions" as used herein means 23° C.±1.0° C. and a relative humidity of 50%±2%.

As used herein, "molecular weight" or "M.Wt." refers to the weight average molecular weight unless otherwise stated. Molecular weight is measured using industry standard method, gel permeation chromatography ("GPC").

"Length" as used herein, with respect to a fibrous element, means the length along the longest axis of the fibrous element from one terminus to the other terminus. If a fibrous element has a kink, curl or curves in it, then the length is the length along the entire path of the fibrous element from one terminus to the other terminus.

"Diameter" as used herein, with respect to a fibrous element, is measured according to the Diameter Test Method described herein. In one example, a fibrous element of the present invention exhibits a diameter of less than 100 μm and/or less than 75 μm and/or less than 50 μm and/or less than 25 μm and/or less than 20 μm and/or less than 15 μm and/or less than 10 μm and/or less than 6 μm and/or greater than 1 μm and/or greater than 3 μm.

"Triggering condition" as used herein in one example means anything, as an act or event, that serves as a stimulus and initiates or precipitates a change in the fibrous element and/or particle and/or fibrous structure of the present invention, such as a loss or altering of the fibrous element's and/or fibrous structure's physical structure and/or a release of an additive, such as an active agent therefrom. In another example, the triggering condition may be present in an environment, such as water, when a fibrous element and/or particle and/or fibrous structure of the present invention is added to the water. In other words, nothing changes in the water except for the fact that the fibrous element and/or fibrous structure of the present invention is added to the water.

"Morphology changes" as used herein with respect to a fibrous element's and/or particle's morphology changing means that the fibrous element experiences a change in its physical structure. Non-limiting examples of morphology changes for a fibrous element and/or particle of the present invention include dissolution, melting, swelling, shrinking, breaking into pieces, exploding, lengthening, shortening, and combinations thereof. The fibrous elements and/or particles of the present invention may completely or substantially lose their fibrous element or particle physical structure or they may have their morphology changed or they may retain or substantially retain their fibrous element or particle physical structure as they are exposed to conditions of intended use.

"By weight on a dry fibrous element basis" and/or "by weight on a dry particle basis" and/or "by weight on a dry fibrous structure basis" means the weight of the fibrous element and/or particle and/or fibrous structure, respectively, measured immediately after the fibrous element and/or particle and/or fibrous structure, respectively, has been conditioned in a conditioned room at a temperature of 23° C.±1.0° C. and a relative humidity of 50%±10% for 2 hours. In one example, by weight on a dry fibrous element basis and/or dry particle basis and/or dry fibrous structure basis means that the fibrous element and/or particle and/or fibrous structure comprises less than 20% and/or less than 15% and/or less than 10% and/or less than 7% and/or less than 5% and/or less than 3% and/or to 0% and/or to greater than 0% based on the dry weight of the fibrous element and/or particle and/or fibrous structure of moisture, such as water, for example free water, as measured according to the Water Content Test Method described herein.

"Total level" as used herein, for example with respect to the total level of one or more active agents present in the fibrous element and/or particle and/or fibrous structure, means the sum of the weights or weight percent of all of the subject materials, for example active agents. In other words, a fibrous element and/or particle and/or fibrous structure may comprise 25% by weight on a dry fibrous element basis and/or dry particle basis and/or dry fibrous structure basis of an anionic surfactant, 15% by weight on a dry fibrous element basis and/or dry particle basis and/or dry fibrous structure basis of a nonionic surfactant, 10% by weight of a chelant on a dry fibrous element basis and/or dry particle basis and/or dry fibrous structure basis, and 5% by weight of a perfume a dry fibrous element basis and/or dry particle basis and/or dry fibrous structure basis so that the total level of active agents present in the fibrous element and/or particle and/or fibrous structure is greater than 50%; namely 55% by weight on a dry fibrous element basis and/or dry particle basis and/or dry fibrous structure basis.

"Fibrous structure product" as used herein means a solid form, for example a rectangular solid, sometimes referred to as a sheet, that comprises one or more active agents, for example a fabric care active agent, a dishwashing active agent, a hard surface active agent, and mixtures thereof. In one example, a fibrous structure product of the present invention comprises one or more surfactants, one or more enzymes (such as in the form of an enzyme prill), one or more perfumes and/or one or more suds suppressors. In another example, a fibrous structure product of the present invention comprises a builder and/or a chelating agent. In another example, a fibrous structure product of the present invention comprises a bleaching agent (such as an encapsulated bleaching agent).

"Associate," "Associated," "Association," and/or "Associating" as used herein with respect to fibrous elements and/or particle means combining, either in direct contact or in indirect contact, fibrous elements and/or particles such that a fibrous structure is formed. In one example, the associated fibrous elements and/or particles may be bonded together for example by adhesives and/or thermal bonds. In another example, the fibrous elements and/or particles may be associated with one another by being deposited onto the same fibrous structure making belt and/or patterned belt.

"Ply" or "Plies" as used herein means an individual fibrous structure optionally to be disposed in a substantially contiguous, face-to-face relationship with other plies, forming a multiple ply fibrous structure. It is also contemplated that a single fibrous structure can effectively form two "plies" or multiple "plies", for example, by being folded on itself.

As used herein, the articles "a" and "an" when used herein, for example, "an anionic surfactant" or "a fiber" is understood to mean one or more of the materials that is claimed or described.

As used herein, the terms "include," "includes," and "including," are meant to be non-limiting.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise noted, all component or composition levels are in reference to the active level of that component or composition, and are exclusive of impurities, for example, residual solvents or by-products, which may be present in commercially available sources.

Fibrous Structure

The fibrous structure of the present invention comprises a plurality of fibrous elements, for example a plurality of filaments, and one or more particles, for example one or more active agent-containing particles, such as water-soluble, active agent-containing particles.

The fibrous structure can be include: matrix particles containing perfume ingredients and fibrous elements containing (a) from about 1 wt % to about 50 wt % polymeric structurant; (b) from about 10 wt % to about 85 wt % of a high melting point fatty compound such as a fatty amphiphile, and (c) from about 1 wt % to about 60 wt % of a cationic surfactant. When water is added to the fibrous structure at a ratio of about 5:1 a lamellar structure can be formed.

In one example, the fibrous elements and/or particles may be arranged within the fibrous structure to provide the fibrous structure with two or more regions that comprise different active agents. For example, one region of the fibrous structure may comprise bleaching agents and/or surfactants and another region of the fibrous structure may comprise softening agents.

As shown in FIG. 4, an example of a fibrous structure 28 according to the present invention comprises a first layer 30 comprising a plurality of fibrous elements 32, in this case filaments, a second layer 34 comprising a plurality of fibrous elements 32, in this case filaments, and a plurality of particles 36 positioned between the first and second layers 30 and 34. The plurality of particles 36 can contain perfume. A similar fibrous structure can be formed by depositing a plurality of particles on a surface of a first ply of fibrous structure comprising a plurality of fibrous elements and then associating a second ply of fibrous structure comprising a plurality of fibrous elements such that the particles are positioned between the first and second plies.

Figure 5:
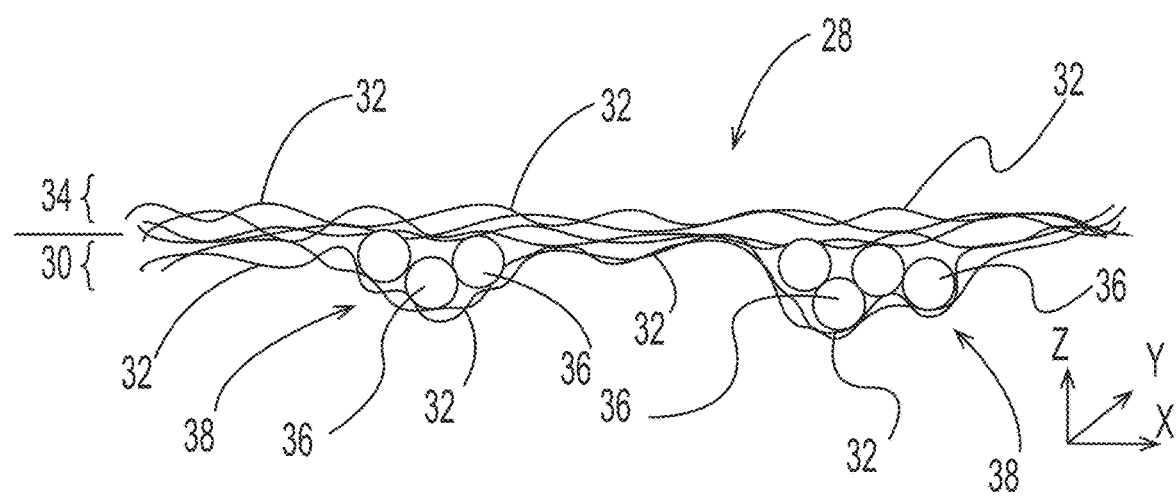
FIGS. 5 and 6 are schematic representations of cross-sectional views of other examples of fibrous structures according to the present invention.

As shown in FIG. 5, another example of a fibrous structure 28 of the present invention comprises a first layer 30 comprising a plurality of fibrous elements 32, in this case filaments, wherein the first layer 30 comprises one or more pockets 38 (also referred to as recesses), which may be in a non-random, repeating pattern. One or more of the pockets 38 may contain one or more particles 36. The fibrous structure 28 further comprises a second layer 34 that is associated with the first layer 30 such that the particles 36 are entrapped in the pockets 38. Like above, a similar fibrous structure can be formed by depositing a plurality of particles in pockets of a first ply of fibrous structure comprising a plurality of fibrous elements and then associating a second ply of fibrous structure comprising a plurality of fibrous elements such that the particles are entrapped within the pockets of the first ply. In one example, the pockets may be separated from the fibrous structure to produce discrete pockets.

Figure 6:
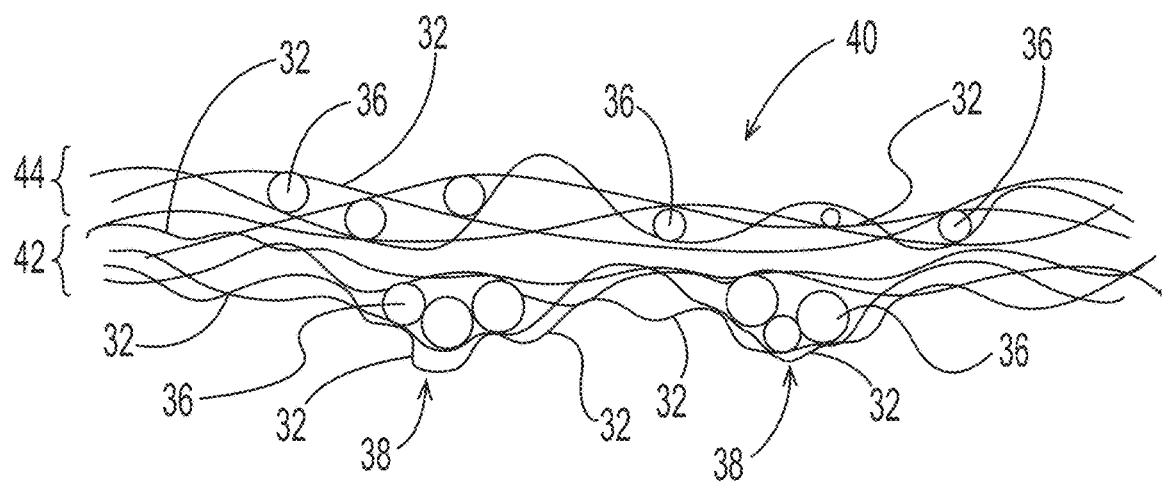

As shown in FIG. 6, an example of a multi-ply fibrous structure 40 of the present invention comprises a first ply 42 of a fibrous structure according to FIG. 5 above and a second ply 44 of fibrous structure associated with the first ply 42, wherein the second ply 44 comprises a plurality of fibrous elements 32, in this case filaments, and a plurality of particles 36 dispersed, in this case randomly, in the x, y, and z axes, throughout the fibrous structure.

Figure 7:
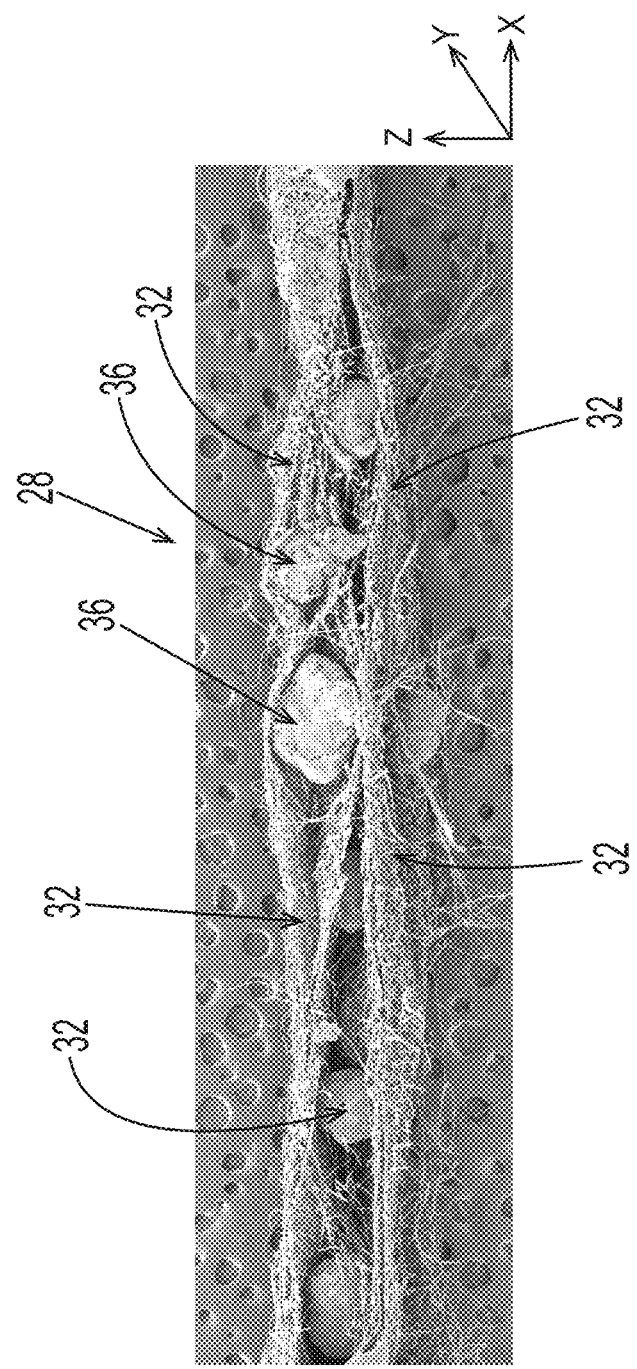
FIG. 7 is a schematic representation of a cross-sectional view of another example of a fibrous structure according to the present invention.

As shown in FIG. 7, an example of a fibrous structure 28 of the present invention comprises a plurality of fibrous elements 32, in this case filaments, and a plurality of particles 36 dispersed, in this case randomly, in the x, y, and z axes, throughout the fibrous structure 28.

Even though the fibrous element and/or fibrous structure of the present invention are in solid form, the filament-forming composition used to make the fibrous elements of the present invention may be in the form of a liquid.

In one example, the fibrous structure comprises a plurality of identical or substantially identical from a compositional perspective of fibrous elements according to the present invention. In another example, the fibrous structure may comprise two or more different fibrous elements according to the present invention. Non-limiting examples of differences in the fibrous elements may be physical differences such as differences in diameter, length, texture, shape, rigidity, elasticity, and the like; chemical differences such as crosslinking level, solubility, melting point, Tg, active agent, polymeric structurant, color, level of active agent, basis weight, level of polymeric structurant, presence of any coating on fibrous element, biodegradable or not, hydrophobic or not, contact angle, and the like; differences in whether the fibrous element loses its physical structure when the fibrous element is exposed to conditions of intended use; differences in whether the fibrous element's morphology changes when the fibrous element is exposed to conditions of intended use; and differences in rate at which the fibrous element releases one or more of its active agents when the fibrous element is exposed to conditions of intended use. In one example, two or more fibrous elements and/or particles within the fibrous structure may comprise different active agents. This may be the case where the different active agents may be incompatible with one another, for example an anionic surfactant (such as a shampoo active agent) and a cationic surfactant (such as a hair conditioner active agent).

In another example, the fibrous structure may exhibit different regions, such as different regions of basis weight, density and/or caliper. In yet another example, the fibrous structure may comprise texture on one or more of its surfaces. A surface of the fibrous structure may comprise a pattern, such as a non-random, repeating pattern. The fibrous structure may be embossed with an emboss pattern. In another example, the fibrous structure may comprise apertures. The apertures may be arranged in a non-random, repeating pattern.

The fibrous structure of the present invention may be used as is or may be coated with one or more active agents.

In one example, the fibrous structure of the present invention exhibits a thickness of greater than 0.01 mm and/or greater than 0.05 mm and/or greater than 0.1 mm and/or to about 100 mm and/or to about 50 mm and/or to about 20 mm and/or to about 10 mm and/or to about 5 mm and/or to about 2 mm and/or to about 0.5 mm and/or to about 0.3 mm as measured by the Thickness Test Method described herein.

Non-limiting examples of product type embodiments for use by the structure can include hair conditioner structures, hand cleansing structures, hair shampoo or other hair treatment structures, including combination hair shampoo and conditioner structures.

For fibrous structures, the structure can comprise a significant number of dissolvable fibers with an average diameter less than about 150 micron, alternatively less than about 100 micron, alternatively less than about 10 micron, and alternatively less than about 1 micron with a relative standard deviation of less than 100%, alternatively less than 80%, alternatively less than 60%, alternatively less than 50%, such as in the range of 10% to 50%, for example. As set forth herein, the significant number means at least 10% of all the dissolvable fibers, alternatively at least 25% of all the dissolvable fibers, alternatively at least 50% of all the dissolvable fibers, alternatively at least 75% of all the dissolvable fibers. The significant number may be at least 99% of all the dissolvable fibers. Alternatively, from about 50% to about 100% of all the dissolvable fibers may have an average diameter less than about 10 microns. The dissolvable fibers produced by the method of the present disclosure can have a significant number of dissolvable fibers with an average diameter less than about 1 micron, or sub-micron fibers. In an embodiment, fibrous structure may have from about 25% to about 100% of all the dissolvable fibers with an average diameter less than about 1 micron, alternatively from about 35% to about 100% of all the dissolvable fibers with an average diameter less than about 1 micron, alternatively from about 50% to about 100% of all the dissolvable fibers with an average diameter less than about 1 micron, and alternatively from about 75% to about 100% of all the dissolvable fibers with an average diameter less than about 1 micron.

The structure can be characterized in one aspect by its Specific Surface Area. The structure can have a Specific Surface Area of from about 0.03 $m^2/g$ to about 0.25 $m^2/g$, alternatively from about 0.035 $m^2/g$ to about 0.22 $m^2/g$, alternatively from about 0.04 $m^2/g$ to about 0.19 $m^2/g$, and alternatively from about 0.045 $m^2/g$ to about 0.16 $m^2/g$.

The structure can be a flat, flexible structure in the form of a pad, a strip, or tape and having a thickness of from about 0.5 mm to about 10 mm, alternatively from about 1 mm to about 9 mm, alternatively from about 2 mm to about 8 mm, and alternatively from about 3 mm to about 7 mm as measured by the below methodology. The Structure can be a sheet having a thickness from about 5 mm to about 6.5 mm. Alternatively, two or more sheets are combined to form a Structure with a thickness of about 5 mm to about 10 mm.

The structure can have a basis weight of from about 200 grams/$m^2$ to about 2,000 grams/$m^2$, alternatively from about 400 g/$m^2$ to about 1,200 g/$m^2$, alternatively from about 600 g/$m^2$ to about 2,000 g/$m^2$, and alternatively from about 700 g/$m^2$ to about 1,500 g/$m^2$.

The structure can have a dry density of from about 0.08 g/$cm^3$ to about 0.40 g/$cm^3$, alternatively from about 0.08 g/$cm^3$ to about 0.38 g/$cm^3$, alternatively from about 0.10 g/$cm^3$ to about 0.25 g/$cm^3$, and alternatively from about 0.12 g/$cm^3$ to about 0.20 g/$cm^3$.

Non-limiting examples of other fibrous structures suitable for the present invention are disclosed in U.S. Pat. Nos. 8,980,816 and 9,139,802 and U.S. Pub. No. 2013/0171421 are hereby incorporated by reference herein.

Particles

Figure 11:
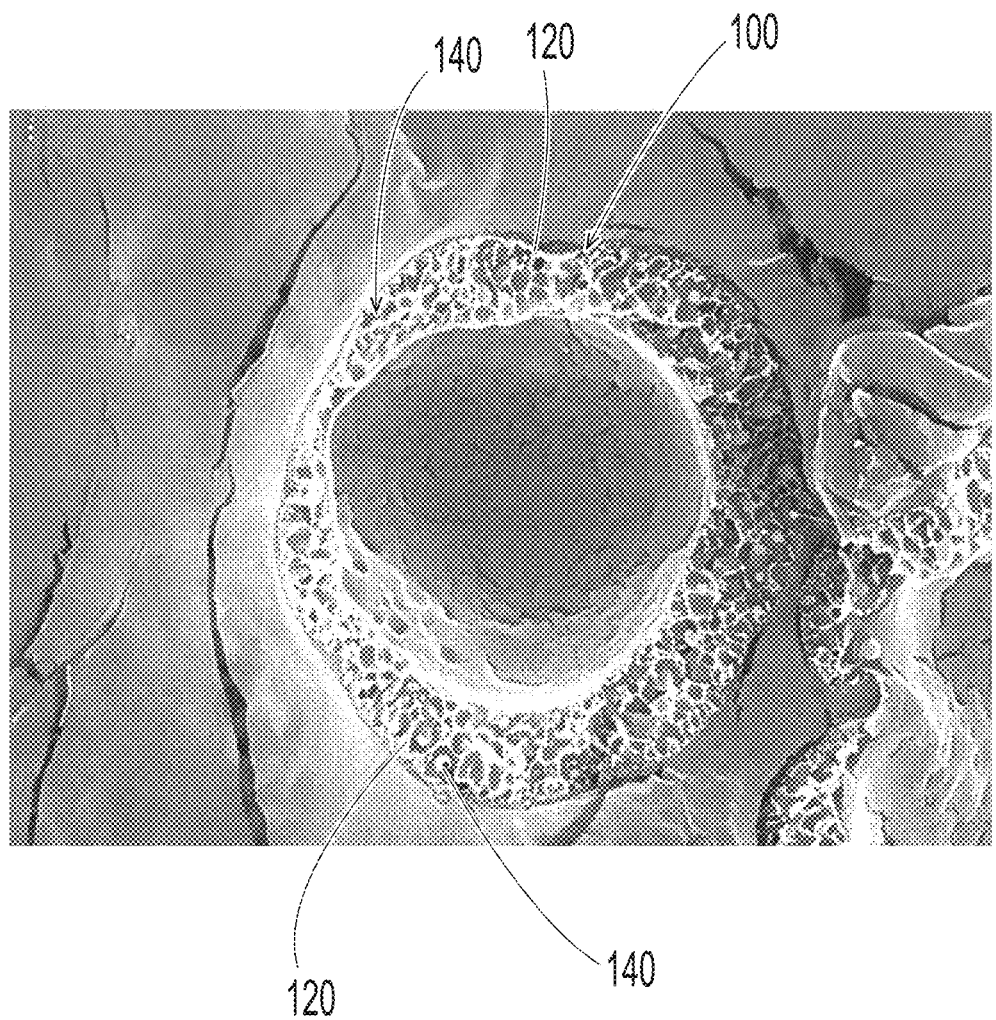
FIG. 11 is a scanning electron microscope SEM cross-section of an example of a matrix particle according to the present invention.
Figure 12:
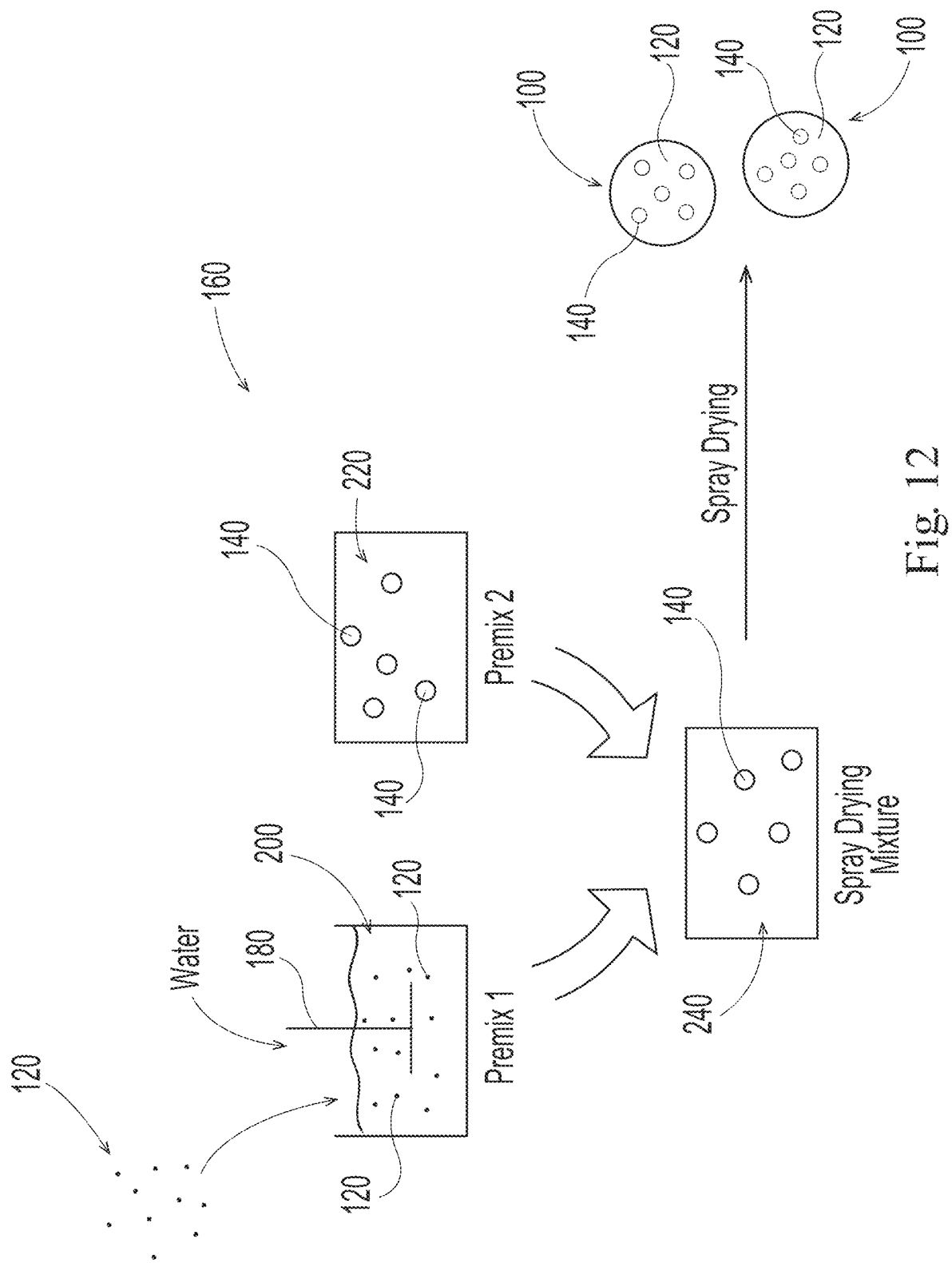
FIG. 12 is a schematic representation of an example of a process for making a matrix particle according to the present invention.

The particles can be matrix particles. As shown in FIG. 11, an example of a matrix particle 100 of the present invention comprises one or more matrix materials 120 and one or more hydrophobic active agents 140 dispersed throughout the one or more matrix materials 120. As seen in FIG. 11, this example of a matrix particle 100 is a hollow matrix particle.

The matrix particles may be water-soluble or water-insoluble. In one example, one group of particles may be water-soluble, and a different group of particles may be water-insoluble. In one example, the hydrophobic benefit agent, such as perfume, can be released from the matrix particle upon the matrix particle contacting a polar solvent, for example water. In another example, the particles can be water-insoluble.

The matrix design of the particles can result in more robust particles, even if there is some fracture of particles, only that portion of the particle releases the hydrophobic active (e.g. perfume oil), the remaining portions of the fractured matrix particle retains its hydrophobic active agents until exposed to conditions that trigger release and/or are fractured again. This ability of the matrix particles to fracture but have portions of the matrix particle retain its hydrophobic active agents is advantageous vs. vs. core/shell capsules wherein fracture of the particle results in total loss of the hydrophobic benefit agent.

The matrix particles can have a leakage of less than or equal to 20%, alternatively less than or equal to 18%, alternatively less than or equal to 16%, alternatively less than or equal to 15%, alternatively less than or equal to 13%, alternatively less than or equal to 10%, alternatively less than or equal to 8%, alternatively less than or equal to 6%, alternatively less than or equal to 5%, alternatively less than or equal to 4%, alternatively less than or equal to 3%, alternatively less than or equal to 2%, and/or alternatively less than or equal to 1%, according to the Analysis of Free Perfume in Perfume Particles described hereafter.

The particle can contain one or more hydrophobic benefit agent and one or more matrix materials. The one or more matrix materials can be selected for the matrix particle based upon their compatibility with the one or more hydrophobic active agents.

The particle can contain from about 10 wt % to about 90 wt % of a hydrophobic benefit agent, alternatively from about 15 wt % to about 70 wt %, alternatively from about 20 wt % to about 50 wt %, and alternatively from about 30 wt % to about 45 wt %, by total weight of the particles. The hydrophobic benefit agent can be a nonpolar material. The hydrophobic benefit agent can include a perfume, an essential oil, an oil, a vitamin oil, a vegetable oil, a silicone, shea butter, cocoa butter, petrolatum, and combinations thereof. In one example, the hydrophobic benefit agent can be a perfume. In another example, the hydrophobic benefit agent can include a perfume in combination with a silicone, such as a terminal aminosilicone, and/or oligomeric vegetable oils. In another example, the hydrophobic benefit agent can include a combination of perfumes.

The perfume can include compositions comprising materials having an Log P (logarithm of octanol-water partition coefficient) of from about 2 to about 12, from about 2.5 to about 8, or even from about 2.5 to about 6 and a boiling point of less than about 280° C., from about 50° C. to about less than about 280° C., from about 50° C. to about less than about 265° C., or even from about 80° C. to about less than about 250° C.; and optionally, an ODT (odor detection threshold) of less than about 100 parts per billion (ppb), from about 0.00001 ppb to about less than about 100 ppb, from about 0.00001 ppb to about less than about 50 ppb or even from about 0.00001 ppb to about less than about 20 ppb.

A wide variety of natural and synthetic chemical ingredients useful as perfumes and/or perfumery ingredients include but not limited to aldehydes, ketones, esters, and mixtures thereof. Non-limiting examples of essential oils can include those obtained from orange oil, lemon oil, thyme, lemongrass, citrus, anise, clove, aniseed, rose extract, lavender, citronella, *eucalyptus*, peppermint, camphor, sandalwood, cinnamon leaf, cedar, pine oil, musk, patchouli, balsamic essence, and combinations thereof. Essential oils that exhibit antimicrobial properties are also contemplated by this invention.

Non-limiting examples of vitamin oils can include fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials.

Non-limiting examples of vegetable oils can include but are not limited to oils derived from palm, corn, canola, sunflower, safflower, rapeseed, castor, olive, soybean, coconut and the like in both the unsaturated forms and hydrogenated forms, and mixtures thereof.

A diluent can be mixed with the hydrophobic benefit agent. Diluents can be miscible in the hydrophobic benefit agent, such as perfume oil, and can act to reduce the volatility of the fragrance oil. Non-limiting examples of diluents can include isopropyl myristate, iso E super, triethyl citrate, vegetable oils, hydrogenated oils, and combinations thereof.

In one example, the hydrophobic active agent may comprise a water-insoluble particle, such as silica, effervescent particles, such as an effervescent acid, for example citric acid, and/or an effervescent salt, for example sodium bicarbonate, titanium dioxide, and/or sodium hexametaphosphate (commonly referred to as Glass H®), and mixtures thereof.

In one example, the hydrophobic active agents exhibit a particle and/or droplet size of at least 0.02 μm to about 200 μm and/or at least 0.1 μm to about 100 μm and/or from about 0.5 μm to about 75 μm and/or from about 1 μm to about 50 μm and/or from about 1 μm to about 30 μm and/or from about 2 μm to about 15 μm and/or from about 5 μm to about 10 μm. The droplet size of the hydrophobic active agents can be measured by any suitable method know in the art. For example, the droplet size of the hydrophobic active agents may be measured prior to making the matrix particle for example when the hydrophobic active agent is present as droplets in an emulsion and/or the droplet size of the hydrophobic active agents may be measured by dissolving in water the matrix material of the matrix particle leaving the hydrophobic active agent droplets within the water.

In one example, when the matrix particle is a water-insoluble matrix particle, for example comprises one or more hydrophobic active agents, for example a perfume and/or a silicone, the one or more hydrophobic active agents releases from the matrix particle upon the matrix particle contacting a polar solvent, which swells the matrix particle and facilitates diffusion, for example increases diffusion of the one or more hydrophobic active agents out of the water-insoluble matrix particle. The diffusion of the one or more hydrophobic active agents may not be complete or fast.

The particle can contain from about 10 wt % to about 90 wt % of a matrix material, alternatively from about 30 wt % to about 85 wt %, alternatively from about 40 wt % to about 85 wt %, alternatively from about 45 wt % to about 80 wt %, alternatively from about 50 wt % to about 75 wt %, by total weight of the particles.

The particle can comprise a matrix material selected from the group consisting of water-soluble polymers, polyvinyl alcohol, polysaccharides, crosslinking agents, catalysts, polyethylene glycols (PEG), starches, gums, gelatin, dextrins, as well as hydrolyzed gums and hydrolyzed gelatin, and combinations thereof. Non-limiting examples of starches can include gum arabic, larch, pectin, tragacanth, locust bean, guar, alginates such as sodium alginate and propylene glycol alginates, carrageenans, cellulose gums such as carboxymethyl cellulose, and karaya. Non-limiting examples of water-soluble polymers can include polyacrylic acid and its copolymers, polyvinylpyrrolidone and its copolymers, polyacrylamide and its copolymers, polyvinylethyl ether, polyethyleneimine, polymethacrylic acid, other water soluble acrylic polymers such as N-isopropyl acrylamide, N—N-dimethylacrylamide, polyvinyloxoazolidone, polycaprolactam, polystyrene sulfonate, polyvinyl formamide, polyvinyl amine, alkylated vinyl pyrrolidone, vinyl caprolactam, vinyl valerolactam, vinyl imidazole, acrylic acid, methacrylate, acrylamide, methacrylamide, dimethacrylamide, alkylaminomethacrylate, and alkylaminomethacrylamide monomers, and combinations thereof.

Suitable matrix materials can include dextrins, especially carboxylated dextrins derived from oxidized starches containing a controlled amount of carboxyl groups. These carboxylated dextrins can be prepared from oxidized cereal starches such as corn, wheat, waxy maize and waxy sorghum starches. Carboxylated dextrins derived from oxidized root starches, such as tapioca and potato starches, may also be employed where desired by the practitioner. All of these carboxylated dextrins can be compatible with volatile oils, like perfumes.

The matrix material can contain polyethylene glycol (PEG). The PEG can have a molecular weight from about 4000 to about 10,000 g/mol, alternatively from about 6000 to about 9,000 g/mol, and alternatively from about 7000 to about 8000 g/mol. Alternatively, the PEG can have a molecular weight from about 4000 to about 8000 g/mol. The PEG can be solid at room temperature with a melting point of about 60° C. In one example, the particle can contain PEG 8000. In one example a particle with perfume can be formed, including a perfume microcapsule (PMC) or a matrix particle and then it can be coated with PEG. Additional information on PMC is found at US 2018/0223225 hereby incorporated by reference herein.

The matrix material can include a polysaccharide that can be present in an amount effective to provide the desired structural and release properties, for instance from about 5 wt % or 10 wt % or 21 wt % or 25 wt % to 50 wt % or 64 wt % or 72 wt % or 80 wt %, by total weight of the particle.

The polysaccharide can be selected from the group consisting of octenyl succinic acid anhydride modified starch including modified corn starch, gum arabic, xanthan gum, gellan gum, pectin gum, konjac gum and carboxyalkyl cellulose, and combinations thereof.

In one example, the particle can contain from about 10-70 wt. % of a hydrophobic benefit agent, about 21 wt % to about 72 wt % matrix material, such as polysaccharide, from about 3.80 wt % to about 12 wt % crosslinking agent, and from about 1 wt % to about 6 wt % of a catalyst, by total weight of the particle.

The crosslinking agent, when present, can be present in an amount effective (in the presence of the catalyst) to crosslink the material, for example polysaccharide, such as starch, to an extent effective to provide the particles with desired durability. The amount can be, e.g., from 1 wt % or 2 wt % or 3.80 wt % or 5 wt % to 8 wt % or 10 wt % or 12 wt % or 15 wt %, by total weight of the particle.

The crosslinking agent can be selected from the group consisting of dimethyldihydroxy urea, dimethyloldihhyrodyethylene urea, dimethylol urea, dihydroxyethylene urea, dimethylolethylene urea, dimethyldihydroxyethylene urea, citric acid, tartaric acid, malic acid, succinic acid, glutaric acid, citraconic acid, itaconic acid, tartrate monosuccinic acid, maleic acid, poly(acrylic acid), poly(methacrylic acid), poly(maleic acid), poly(methylvinylether-co-maleate) copolymer, copolymers of acrylic acid and copolymers of maleic acid, and combinations thereof.

The matrix materials can further contain a catalyst in an amount effective to catalyze the crosslinking of the matrix material, for example polysaccharide, such as starch, to an extent effective to provide the particles with desired durability. The amount can be, e.g., from 0.1 wt % or 0.5 wt % or 1 wt % or 2 wt % to 2.5 wt % or 5 wt % or 6 wt % or 7 wt %, by total weight of the particle.

The catalyst can be a reducing agent and/or electron donor and can be selected from the group consisting of ammonium chloride, ammonium sulfate, aluminum chloride, magnesium chloride, magnesium nitrate, sodium hypophosphite, and combinations thereof.

It can be common to add a silica flow aid to particles, including matrix particles and encapsulated particles. The silica flow aid can include precipitated silica, fumed silica, hydrophobic silica, and combinations thereof. However, adding a silica flow aid can prevent agglomeration of the particles. Therefore, the particles can be free of and/or substantially free of a silica flow aid. In another example the particles can contain less than 1 wt %, less than 0.5 wt %, less than 0.1 wt %, and/or less than 0.05 wt % silica flow aid, by total weight of the particle. The particles of the invention can be provided by a method comprising: mixing the hydrophobic benefit agent with the matrix material, such as the polysaccharide, and water to provide an emulsion; agitating the emulsion to provide a modified emulsion containing hydrophobic benefit agent ingredient droplets with a volume average diameter of less than 5 microns; optionally mixing with the modified emulsion the crosslinking agent and the catalyst to provide a spray-ready emulsion; optionally spray drying the spray-ready emulsion to provide a powder; and optionally heating the modified powder to form the controlled release particles.

Optionally, a desiccant can be added to the powder to absorb the moisture that is released from the particle during heating, such that the moisture does not act to plasticize the particle and form large aggregates. Suitable desiccants include but are not limited to calcium sulfate, sodium sulfate, calcium silicate, hydrophilic aluminosilicates, magnesium sulfate, silica gel, crosslinked polyacrylates, and the like. It can be desirable to have the desiccant particle size at least 5 times the median particle size of the powder being heated, such that after the powder heating process, the desiccants can be removed via sieving. The amount can be, e.g., from 0.05 wt. % or 0.10 wt. % or 0.5 wt. % or 1 wt. % to 2.5 wt. % or 5 wt. % or 7.5 wt. % or 10 wt. %, by total weight of the particle.

In one example, the matrix particle exhibits a size of less than 500 µm and/or less than 400 µm and/or less than 300 µm and/or less than 200 µm and/or less than 100 µm and/or to about 20 µm and/or to about 30 µm and/or from about 20 µm to about 500 µm and/or from about 20 µm to about 400 µm and/or from about 20 µm to about 300 µm and/or from about 20 µm to about 200 µm and/or from about 20 µm to about 100 µm and/or from about 20 to about 90 µm and/or from about 30 µm to about 80 µm as measured according to the Median Particle Size Test Method described herein.

Non-limiting examples of other particles including matrix particles containing polysaccharides are disclosed in U.S. Pat. No. 4,276,312 and U.S. Pub. No. 2017/0360676 are hereby incorporated by reference herein.

Process for Making Matrix Particles

In one example, as shown in FIG. 11, the matrix particles 100 of the invention may be made by a process 160 comprising the steps of:
 a. dissolving one or more matrix materials 120 in water, for example distilled water, with stirring, for example by an overhead strirrer 180, and heating the one or more matrix materials 120 in the water, for example to about 90° C., to help facilitate dissolution of the one or more matrix materials 120 to form a solution 200, for example Premix 1;
 b. providing an emulsion comprising one or more hydrophobic active agents 140 and water with a silicone content of 20%, or making an emulsion 220 by adding one or more hydrophobic active agents 140 in water, for example distilled water, with or without an emulsifying agent, to form the emulsion 220, for example Premix 2;
 c. mixing the solution from Step a with the emulsion from Step b to form a spray drying mixture 240 comprising the solution from Step a and the emulsion comprising hydrophobic active agents 140 from Step b; and
 d. spray drying the spray drying mixture 240 to form matrix particles 100 comprising one or more matrix materials 120 and one or more hydrophobic active agents 140.

In another example, the matrix particles 10 of the invention may be made by a process comprising the steps of:
 a. mixing one or more hydrophobic active agents with one or more matrix materials in the presence of water to provide an emulsion;
 b. agitating the emulsion to provide a modified emulsion containing hydrophobic active agent droplets, for example hydrophobic active agent droplets with a volume average diameter of less than 5 µm; and
 c. producing matrix particles comprising the one or more matrix materials and the one or more hydrophobic active agents dispersed throughout the matrix materials from the modified emulsion.

The step of producing matrix particles may comprise one or more of the following optional steps:
 d. optionally adding to the modified emulsion a crosslinking agent and/or catalyst to provide a spray-ready emulsion;
 e. optionally spray drying the spray-ready emulsion to provide a modified powder, which when dried forms the matrix particles; and
 f. optionally heating the modified powder to form the matrix particles.

Optionally, a desiccant can be added to the modified powder to absorb any moisture that may be released from the matrix particle during heating, such that the moisture does not act to plasticize the matrix particle and form large aggregates (greater than 2000 µm). Suitable desiccants include but are not limited to calcium sulfate, sodium sulfate, calcium silicate, hydrophilic aluminosilicates, magnesium sulfate, silica gel, crosslinked polyacrylates, and the like. It can be desirable to have the desiccant particle size at least 5 times the median particle size of the modified powder being heated, such that after the modified powder heating process, the desiccants can be removed via sieving. The amount of desiccant, when present, can be for example at least about 0.05 wt. % and/or at least about 0.10 wt. % and/or at least about 0.5 wt. % and/or at least about 1 wt. % and/or to about 10 wt. % and/or to about 7 wt. % and/or to about 5 wt. % and/or to about 2.5 wt. % by total weight of the matrix particle.

In another example of the present invention, which is shown in FIG. 11 with the exception of Premix 2, which in this example is replaced with neat hydrophobic active agent particles, for example water-insoluble hydrophobic active agent particles such as silica, wherein the matrix particles 100 are made by a process 160 comprising the steps of:

a. dissolving one or more matrix materials 120 in water, for example distilled water, with stirring, for example by an overhead stirrer 180, and heating the one or more matrix materials 120 in the water, for example to about 90° C., to help facilitate dissolution of the one or more matrix materials 120 to form a solution 200, for example Premix 1;

b. adding one or more hydrophobic active agents, for example one or more hydrophobic active agent particles, 140;

c. mixing the solution from Step a with the hydrophobic active agents from Step b to form a spray drying mixture 240 comprising the solution from Step a and the hydrophobic active agents 140 from Step b; and d. spray drying the spray drying mixture 240 to form matrix particles 100 comprising one or more matrix materials 120 and one or more hydrophobic active agents 140, for example one or more hydrophobic active agent particles.

In one example, the matrix particles of the present invention are made using the methods and/or equipment described in U.S. Pat. Nos. 8,939,388, 9,332,776, 9,551,527, 9,861, 945, and/or 9,993,787 all of which are incorporated herein by reference.

Agglomerated Particles

The particles can be agglomerated to form agglomerated particles, for example agglomerated particles suitable for use in fibrous structures. It can be beneficial to form agglomerates because when the particles are too small they fall through the fibrous web and/or are easily knocked off the outer surfaces of the fibrous structure. However, if the particles are too large, they are noticeable, and the consumer complains that the dissolvable structure feels gritty during use.

Agglomeration also aids in maintaining consistent formulation of the finished product when multiple smaller matrix particles are used in one finished fibrous structure. Segregation of particle mixtures is an extremely common problem in solids processing. Agglomerating multiple matrix particles at the correct ratio for the finished product ensures delivery of all actives at the desired level.

The agglomerated particles can be from about 100 microns to about 1500 microns, alternatively 150 microns to about 1250 microns, alternatively from about 200 microns to about 1000 microns, and alternatively from about 300 microns to about 800 microns. Alternatively, the agglomerates can be from about 200 microns to about 500 microns as measured according to the Median Particle Size Test Method described herein.

Agglomerated particle size is controlled by the initial matrix particle size, binder selection, and the time of mixing after binder addition in the agglomeration process. In one example, a matrix particle, for example exhibiting a size of from about 400 µm to about 500 µm as measured according to the Median Particle Size Test Method described herein, is chosen as a "seed particle", the binder, for example a nonionic binder, used to stick to smaller matrix particles, for example matrix particles having a size of from about 50 µm to about 100 µm as measured according to the Median Particle Size Test Method described herein.

The agglomerated particles can be pre-formed before incorporating them into the fibrous web. A binder can be used to aid in, assist in, and/or facilitate agglomerating the particles together.

A binder can be any material or substance that holds or draws other materials together to form a cohesive whole mechanically, chemically, or as an adhesive. Binders can include those that are nonionic to minimize the interaction with the reactants, however, polymeric and ionic binders can also be used. Suitable binders include, but are not limited to, Nonionic surfactants, nonionic polymers, Ethoxylated Alcohols, Sorbitan Derivates, Polyethylene Glycols, Corn Syrup, Paraffin, waxes, Fatty Alcohols, and mixtures thereof. In one example, the binder can be polyvinylpyrrolidone (PVP). Binders can be included in the agglomerated particle at a level of from about 0.05 weight % of the agglomerated particle to about 10 weight % of the agglomerated particle, alternatively from about 1 weight % of the agglomerated particle to about 5 weight % of the agglomerated particle. Binders typically are included at from about 0.05% to about to about 5 weight % of the fibrous structure.

Optionally, a humectant can be added to the agglomerated particle. Suitable humectants can include salts, sugars, acids, glycols, inorganics and combinations thereof. Suitable humectants can be selected from PEG400, PEG 600, Sorbitol, Potassium Carbonate, Sodium Chloride, Potassium Acetate, PEG 4000, zeolite, Corn syrup, Glycerol, Fructose, Sucrose, citric acid, tartaric acid, malic acid, lactic acid, Magnesium Chloride, and combinations thereof. Suitable humectant ranges are from about 0.1 to about 15 weight % of the agglomerated particle, alternatively from about 1 to about 7 weight % of the agglomerated particle. Suitable humectant ranges include from about 0.5 to about 10 weight % of the fibrous structure, alternatively from about 1 to about 7 weight % of the fibrous structure.

Optionally, flow aids can be included at low levels (for example less than about 1 wt. % and/or less than about 0.5 wt. % and/or less than 0.1 wt. % and/or less than about 0.05 wt. % of the agglomerated particle) to help make the agglomerated particle flow better, non-limiting examples include Zeolite A, precipitated silica, precipitated silicates, fly ash, talc, starch, clays, metallic stearates, phosphates, amides, polysaccharides, sugars, and combinations thereof. Particularly suitable materials include Zeolite A, silica, sugars and mixtures thereof.

The perfume particles can be agglomerated with other perfume particles with either the same and/or different perfume ingredients. The perfume particles can also be agglomerated with different particles, such as particles containing effervescent agents, silicones, surfactants, cationic polymers, antimicrobials including antibacterials and antifungals, and combinations thereof.

The agglomerated particles can be distributed or evenly distributed throughout the fibrous structure. The agglomerated particles may be distributed evenly on one layer or throughout multiple layers. For example, one method is having it evenly distributed on all layers of the structure. Alternatively, the agglomerated particle could be distributed through a middle layer, alternatively the agglomerated particle could be distributed only on an external layer outwardly facing layer.

Non-limiting examples of agglomerated particles are disclosed in WO2018/140675 hereby incorporated by reference herein.

In one example, the agglomerated particles exhibit an agglomerate bulk density of less than 700 g/L and/or less than 600 g/L and/or less than 500 g/L and/or less than 400 g/L and/or greater than 25 g/L and/or greater than 50 g/L as measured using the re-pour density measurement method. In this method, the agglomerated particles are dropped 12 inches from a funnel into a cup of known volume. The pile of agglomerated particles above the cup rim is then scrapped away, leaving a completely full cup of agglomerated particles. The mass of the remaining agglomerated particles in the full cup is measured gravimetrically. The bulk density is then found by dividing the mass of the remaining agglomerated particles by the volume of the cup, in this case reported in g/L.

The agglomerated particles can be made as follows. Perfume and optionally humectant can be mixed in a convective or tumbling solids mixer including paddle mixers or v-blenders for approximately 5 minutes. Binder can be added and mixed for an additional 5 min, or longer for larger particles or shorter for smaller particles. Optionally, the flow aid can be added after Agglomerated Particle has reached target size. Mixing continues for approximately another minute. Agglomerated Particle can be transferred into storage vessel until ready for use.

Particle size can be controlled by the initial raw material particle size, binder selection, and the time of mixing after binder addition in agglomeration process.

Fibrous Elements

The fibrous element, such as a filament and/or fiber, of the present invention comprises one or more polymeric structurants. In addition to the polymeric structurants, the fibrous element may further comprise one or more high melting point fatty compounds, one or more surfactants, and optional ingredients. Examples of fibrous elements can be found at U.S. patent application Ser. No. 15/979,961, incorporated by reference.

Polymeric Structurant

To improve the fiber spinning of low viscosity material, such as molten fatty alcohols, fatty quaternary ammonium compounds, fatty acids, etc., a polymeric ingredient called a structurant can be added. The structurant increases the shear and extensional viscosity of the fluid to enable fiber formation. The structurant can be included at a level of from about 1 wt % to about 50 wt %, alternatively from about 1 wt % to about 30 wt %, alternatively from about 1 wt % to about 10 wt %, alternatively from about 2 wt % to about 6 wt %, and alternatively from about 3 wt % to about 5 wt % of the composition. The structurant has a weight average molecular weight of from about 10,000 to about 6,000,000 g/mol. A balance can be struck between concentration and molecular weight, such that when a lower molecular weight species is used, it requires a higher level to result in optimal fiber spinning. Likewise, when a higher molecular species is used, lower levels can be used to achieve optimal fiber spinning. The structurant having a weight average molecular weight of from about 3,000,000 g/mol to about 5,000,000 g/mol in included at a level of from about 3 wt % to about 6 wt %. Alternatively, a structurant having a weight average molecular weight of from about 50,000 g/mol to about 100,000 g/mol can be included at a level of from about 30 wt % to about 50 wt %.

The structurant can be soluble in an oily mixture to enable viscosity build for fiber spinning. In addition, the structurant should also be soluble in water to promote removal and to prevent buildup. Suitable structurants include, but are not limited to, polyvinylpyrrolidone, polydimethylacrylamides, and combinations thereof. These polymers are oil (fatty alcohol, fatty acid, fatty quaternary ammonium compounds) soluble, water soluble, and capable of being produced at high weight average molecular weights. For example, suitable polymers for use are PVP K120 from Ashland Inc., having a weight average molecular weight of about 3,500,000 g/mol is soluble in the oil and water and enables fibers to be formed and collected onto a belt. Additional suitable polymers include copolymers of polyvinylpyrrolidone, such as Ganex® or PVP/VA (weight average molecular weight of about 50,000 g/mol) copolymers from Ashland Inc., also performed as suitable structurants but a higher level was utilized to be effective due to their lower weight average molecular weight. In addition, copolymers of polydimethylacrylamide also function as a suitable structurant. Hydroxyl propyl cellulose can also function as a suitable structurant.

Dispersing Agents

When preparing the fibrous structure, it has been found that the addition of a dispersing agent can greatly increase the wetting, hydration, and dispersion of the conditioner materials. The dispersing agent can be included at a level of from about 1 wt % to about 30 wt % of the composition, alternatively from about 5 wt % to about 15 wt %, and alternatively from about 5 wt % to about 10 wt %. A surfactant from the nonionic class of alkyl glucamides can improve the wetting and hydration when added to the solid conditioner formula. The alkyl glucamide surfactant contains a hydrophobic tail of about 8-18 carbons and a nonionic head group of glucamide. For glucamide, the presence of the amide and hydroxyl groups may provide sufficient polarity that balances the hydrophobic carbon tail in such a way to permit the surfactant's solubility in the conditioner oils and also imparts a rapid dispersion of the conditioner ingredients upon exposure to water. Other similar dispersing agents include, but are not limited to, reverse alkyl glucamides, cocoamidopropyl betaines, alkyl glucoside, cetearyl glucoside, stearyl glucoside, alcohol ethoxylates, glycol stearate, glycol distearate, triethanol amine, cocamide MEAs, lauroylsarcosine salts, polyglyceryl palmitates, polyglyceryl stearates, polyoxyethylene alkyl ethers, and mixtures thereof.

Cationic Surfactant

The fibrous structure can comprise a cationic surfactant can be included at a level of from about 1 wt % to about 60 wt %, alternatively from about 10 wt % to about 50 wt %, alternatively from about 20 wt % to about 40 wt % of the composition.

Cationic surfactant useful herein can be one cationic surfactant or a mixture of two or more cationic surfactants. The cationic surfactant can be selected from the group consisting of, but not limited to: a mono-long alkyl quaternized ammonium salt; a combination of a mono-long alkyl quaternized ammonium salt and a di-long alkyl quaternized ammonium salt; a mono-long alkyl amine; a combination of a mono-long alkyl amine and a di-long alkyl quaternized ammonium salt; and a combination of a mono-long alkyl amine and a mono-long alkyl quaternized ammonium salt, a tertiary amine and combinations thereof.

Mono-Long Alkyl Amine

Mono-long alkyl amine useful herein are those having one long alkyl chain of from 12 to 30 carbon atoms, alternatively from 16 to 24 carbon atoms, alternatively from 18 to 22 alkyl group. Mono-long alkyl amines useful herein also include mono-long alkyl amidoamines Primary, secondary, and tertiary fatty amines are useful.

Suitable for use in the fibrous structure are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines can be used in combination with acids such as $\ell$-glutamic acid, lactic acid, hydrochloric acid, malic acid, succinic acid, acetic acid, fumaric acid, tartaric acid, citric acid, $\ell$-glutamic hydrochloride, maleic acid, and mixtures thereof; alternatively $\ell$-glutamic acid, lactic acid, citric acid, at a molar ratio of the amine to the acid of from about 1:0.3 to about 1:2, alternatively from about 1:0.4 to about 1:1.

Mono-Long Alkyl Quaternized Ammonium Salt

The mono-long alkyl quaternized ammonium salts useful herein are those having one long alkyl chain which has from 12 to 30 carbon atoms, alternatively from 16 to 24 carbon atoms, alternatively a C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

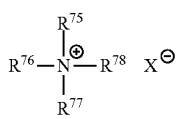

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and X⁻ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, alternatively from 16 to 24 carbon atoms, alternatively from 18 to 22 carbon atoms, alternatively 22 carbon atoms; the remainder of $R^{75}$, $R^{76}$, $R^{77}$ and $R^{78}$ can be independently selected from $CH_3$, $C_2H_5$, $C_2H_4OH$, and mixtures thereof; and X can be selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-Long Alkyl Quaternized Ammonium Salts

When used, di-long alkyl quaternized ammonium salts can be combined with a mono-long alkyl quaternized ammonium salt and/or mono-long alkyl amine salt, at the weight ratio of from 1:1 to 1:5, alternatively from 1:1.2 to 1:5, alternatively from 1:1.5 to 1:4, in view of stability in rheology and conditioning benefits.

Di-long alkyl quaternized ammonium salts useful herein are those having two long alkyl chains of from 12 to 30 carbon atoms, alternatively from 16 to 24 carbon atoms, alternatively from 18 to 22 carbon atoms. Such di-long alkyl quaternized ammonium salts useful herein are those having the formula (I):

wherein two of $R^{71}$, $R^{72}$, $R^{73}$ and $R^{74}$ are selected from an aliphatic group of from 12 to 30 carbon atoms, alternatively from 16 to 24 carbon atoms, alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and X⁻ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Two of $R^{71}$, $R^{72}$, $R^{73}$ and $R^{74}$ can be selected from an alkyl group of from 12 to 30 carbon atoms, alternatively from 16 to 24 carbon atoms, alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Suitable di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention can contain high melting point fatty compound. The high melting point fatty compound can be included in the composition at a level of from about 10 wt % to about 85 wt %, alternatively from 20 wt % to 70 wt %, alternatively from about 50 wt % to about 70 wt %, alternatively from about 10 wt % to about 20 wt % of the composition. The fatty compound can be selected from the group consisting of, but not limited to, fatty amphiphiles, fatty alcohol, fatty acid, fatty amide, fatty ester and combinations thereof.

The high melting point fatty compound useful herein can have a melting point of 25° C. or higher, alternatively 40° C. or higher, alternatively 45° C. or higher, alternatively 50° C. or higher, in view of stability of the emulsion especially the gel matrix. Such melting point is up to about 90° C., alternatively up to about 80° C., alternatively up to about 70° C., alternatively up to about 65° C., in view of easier manufacturing and easier emulsification. The high melting point fatty compound can be used as a single compound or as a blend or mixture of at least two high melting point fatty compounds. When used as such blend or mixture, the above melting point means the melting point of the blend or mixture.

The high melting point fatty compound useful herein can be selected from the group consisting of fatty alcohols, fatty acids, fatty alcohol derivatives, fatty acid derivatives, fatty amides, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound but is done so for convenience of classification and nomenclature. Further, it is understood by the artisan that, depending on the number and position of double bonds, and length and position of the branches, certain compounds having certain required carbon atoms may have a melting point of less than the above. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols can be used in the composition described herein. The fatty alcohols useful herein are those having from about 14 to about 30 carbon atoms, alternatively from about 16 to about 22 carbon atoms. These fatty alcohols are saturated and can be straight or branched chain alcohols.

Suitable fatty alcohols include, but are not limited to, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

Generally, in the mixture, the weight ratio of cetyl alcohol to stearyl alcohol is from about 1:9 to 9:1, alternatively from about 1:4 to about 4:1, alternatively from about 1:2.3 to about 1.5:1.

When using higher level of total cationic surfactant and high melting point fatty compounds, the mixture has the weight ratio of cetyl alcohol to stearyl alcohol of from about 1:1 to about 4:1, alternatively from about 1:1 to about 2:1, alternatively from about 1.2:1 to about 2:1, in view of maintaining acceptable consumer usage. It may also provide more conditioning on damaged part of the hair.

Extensional Aids

The fibrous element can contain an extensional aid. Non-limiting examples of extensional aids can include polymers, other extensional aids, and combinations thereof.

In one example, the extensional aids have a weight-average molecular weight of at least about 500,000 Da. In another example, the weight average molecular weight of the extensional aid is from about 500,000 to about 25,000,000, in another example from about 800,000 to about 22,000,000, in yet another example from about 1,000,000 to about 20,000,000, and in another example from about 2,000,000 to about 15,000,000. The high molecular weight extensional aids are preferred in some examples of the invention due to the ability to increase extensional melt viscosity and reducing melt fracture.

The extensional aid, when used in a meltblowing process, can be added to the composition of the present invention in an amount effective to visibly reduce the melt fracture and capillary breakage of fibers during the spinning process such that substantially continuous fibers having relatively consistent diameter can be melt spun. Regardless of the process employed to produce fibrous elements and/or particles, the extensional aids, when used, can be present from about 0.001% to about 10%, by weight on a dry fibrous element basis and/or dry particle basis and/or dry fibrous structure basis, in one example, and in another example from about 0.005 to about 5%, by weight on a dry fibrous element basis and/or dry particle basis and/or dry fibrous structure basis, in yet another example from about 0.01 to about 1%, by weight on a dry fibrous element basis and/or dry particle basis and/or dry fibrous structure basis, and in another example from about 0.05% to about 0.5%, by weight on a dry fibrous element basis and/or dry particle basis and/or dry fibrous structure basis.

Non-limiting examples of polymers that can be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other extensional aids can include modified and unmodified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Optional Ingredients

The Structure (dried) optionally comprises from about 1 wt % to about 25 wt % plasticizer, in one embodiment from about 3 wt % to about 20 wt % plasticizer, in one embodiment from about 5 wt % to about 15 wt % plasticizer.

When present in the Structures, non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, mannitol, lactitol, isosorbide, glucamine, N-methylglucamine and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyaluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

EP 0283165 B1 discloses suitable plasticizers, including glycerol derivatives such as propoxylated glycerol.

The Structure may comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, antimicrobial agents, sunscreens, tanning agents, exfoliation particles, hair growth or restorer agents, insect repellents, shaving lotion agents, co-solvents or other additional solvents, and similar other materials. Further non-limiting examples of optional ingredients include encapsulated perfumes, such as by β-cyclodextrins, polymer microcapsules, starch encapsulated accords and combinations thereof.

Suitable conditioning agents include high melting point fatty compounds, silicone conditioning agents and cationic conditioning polymers. Suitable materials are discussed in US 2008/0019935, US 2008/0242584 and US 2006/0217288.

Methods of Use

The compositions described herein may be used for cleaning, condition, and/or treating hair, hair follicles, and/or skin including the scalp. The method for treating these consumer substrates may comprise the steps of: a) applying an effective amount of the Structure to the hand, b) wetting the Structure with water to dissolve the solid, c) applying the dissolved material to the target consumer substrate such as to clean, condition, or treat it, and d) rinsing the diluted treatment composition from the consumer substrate. These steps can be repeated as many times as desired to achieve the desired cleansing and or treatment benefit. When the structure is a conditioner, it can be applied before and/or after and/or concurrently with a shampoo.

A method useful for providing a benefit to hair, hair follicles, and/or skin including the scalp, includes the step of applying a composition according to the first embodiment to these target consumer substrates in need of regulating.

Alternatively a useful method for regulating the condition of hair, hair follicles, skin, and/or skin including the scalp, includes the step of applying one or more compositions described herein to these target consumer substrates in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams, alternatively from about 1.0 grams to about 5 grams, and alternatively from about 1.5 grams to about 3 grams.

Product Types and Articles of Commerce

Non-limiting examples of products that utilize the fibrous structure include hand cleansing substrates, hair shampoo, hair conditioner or other hair treatment substrates, body cleansing substrates, shaving preparation substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

Described herein is an article of commerce comprising one or more fibrous structures described herein, and a communication directing a consumer to dissolve the Structure and apply the dissolved mixture to hair, hair follicles, skin including the scalp, to achieve a benefit to the target consumer substrate, a rapidly lathering foam, a rapidly rinsing foam, a clean rinsing foam, a conditioning treatment and combinations thereof. The communication may be printed material attached directly or indirectly to packaging that contains the fibrous structure or on the fibrous structure itself. Alternatively, the communication may be an electronic or a broadcast message that is associated with the article of manufacture. Alternatively, the communication may describe at least one possible use, capability, distinguishing feature and/or property of the article of manufacture.

Exposure to Triggering Condition

The conditioning ingredients, including the cationic surfactant and fatty alcohol, may be released from the fibrous element and/or particle and/or fibrous structure when the fibrous element and/or particle and/or fibrous structure is exposed to a triggering condition. In one example, one or more active agents may be released from the fibrous element and/or particle and/or fibrous structure or a part thereof when the fibrous element and/or particle and/or fibrous structure or the part thereof loses its identity, in other words, loses its physical structure. For example, a fibrous element and/or particle and/or fibrous structure loses its physical structure when the polymeric structurant dissolves, melts or undergoes some other transformative step such that its structure is lost. In one example, the one or more active agents are released from the fibrous element and/or particle and/or fibrous structure when the fibrous element's and/or particle's and/or fibrous structure's morphology changes.

In another example, one or more active agents may be released from the fibrous element and/or particle and/or fibrous structure or a part thereof when the fibrous element and/or particle and/or fibrous structure or the part thereof alters its identity, in other words, alters its physical structure rather than loses its physical structure. For example, a fibrous element and/or particle and/or fibrous structure alters its physical structure when the polymeric structurant swells, shrinks, lengthens, and/or shortens, but retains its filament-forming properties.

In another example, one or more active agents may be released from the fibrous element and/or particle and/or fibrous structure with its morphology not changing (not losing or altering its physical structure).

In one example, the fibrous element and/or particle and/or fibrous structure may release an active agent upon the fibrous element and/or particle and/or fibrous structure being exposed to a triggering condition that results in the release of the active agent, such as by causing the fibrous element and/or particle and/or fibrous structure to lose or alter its identity as discussed above. Non-limiting examples of triggering conditions include exposing the fibrous element and/or particle and/or fibrous structure to solvent, a polar solvent, such as alcohol and/or water, and/or a non-polar solvent, which may be sequential, depending upon whether the filament-forming composition comprises a polar solvent-soluble material and/or a non-polar solvent-soluble material; exposing the fibrous element and/or particle and/or fibrous structure to heat, such as to a temperature of greater than 75° F. and/or greater than 100° F. and/or greater than 150° F. and/or greater than 200° F. and/or greater than 212° F.; exposing the fibrous element and/or particle and/or fibrous structure to cold, such as to a temperature of less than 40° F. and/or less than 32° F. and/or less than 0° F.; exposing the fibrous element and/or particle and/or fibrous structure to a force, such as a stretching force applied by a consumer using the fibrous element and/or particle and/or fibrous structure; and/or exposing the fibrous element and/or particle and/or fibrous structure to a chemical reaction; exposing the fibrous element and/or particle and/or fibrous structure to a condition that results in a phase change; exposing the fibrous element and/or particle and/or fibrous structure to a pH change and/or a pressure change and/or temperature change; exposing the fibrous element and/or particle and/or fibrous structure to one or more chemicals that result in the fibrous element and/or particle and/or fibrous structure releasing one or more of its active agents; exposing the fibrous element and/or particle and/or fibrous structure to ultrasonics; exposing the fibrous element and/or particle and/or fibrous structure to light and/or certain wavelengths; exposing the fibrous element and/or particle and/or fibrous structure to a different ionic strength; and/or exposing the fibrous element and/or particle and/or fibrous structure to an active agent released from another fibrous element and/or particle and/or fibrous structure.

In one example, one or more active agents may be released from the fibrous elements and/or particles of the present invention when a fibrous structure product comprising the fibrous elements and/or particles is subjected to a triggering step such as forming a wash liquor by contacting the fibrous structure product with water.

Method for Making Fibrous Elements

The fibrous elements of the present invention may be made by any suitable process. A non-limiting example of a suitable process for making the fibrous elements is described below.

Figure 8:
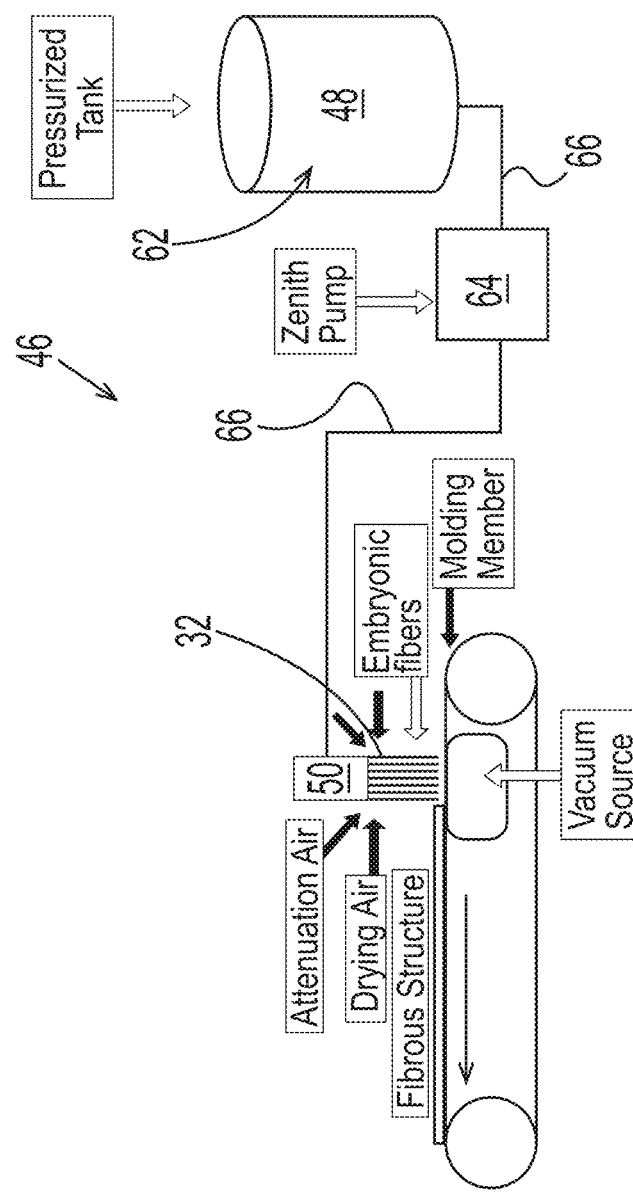
FIG. 8 is a schematic representation of an example of a process for making fibrous elements of the present invention.

In one example, as shown in FIGS. 8 and 9, a method 46 for making a fibrous element 32 according to the present invention comprises the steps of:

a. providing a filament-forming composition 48 comprising one or polymeric structurants, and optionally one or more other ingredients including high melting point fatty compounds and/or one or more surfactants; and b. spinning the filament-forming composition 48, such as via a spinning die 50, into one or more fibrous elements 32, such as filaments, comprising the one or more polymeric structurants and optionally, the one or more other ingredients. The one or more other ingredients may be releasable from the fibrous element when exposed to conditions of intended use. The total level of the one or more polymeric structurants present in the fibrous element 32, may be less than 80% and/or less than 70% and/or less than 65% and/or 50% or less by weight on a dry fibrous element basis and/or dry fibrous structure basis and the total level of the one or more active agents, when present in the fibrous element may be greater than 20% and/or greater than 35% and/or 50% or greater 65% or greater and/or 80% or greater by weight on a dry fibrous element basis and/or dry fibrous structure basis.

As shown in FIG. 9, the spinning die 50 may comprise a plurality of fibrous element-forming holes 52 that include a melt capillary 54 encircled by a concentric attenuation fluid hole 56 through which a fluid, such as air, passes to facilitate attenuation of the filament-forming composition 48 into a fibrous element 32 as it exits the fibrous element-forming hole 52.

In one example, during the spinning step, any volatile solvent, such as water, present in the filament-forming composition 48 is removed, such as by drying, as the fibrous element 32 is formed. In one example, greater than 30% and/or greater than 40% and/or greater than 50% of the weight of the filament-forming composition's volatile solvent, such as water, is removed during the spinning step, such as by drying the fibrous element being produced.

The filament-forming composition may comprise any suitable total level of polymeric structurant and any suitable level of active agents so long as the fibrous element produced from the filament-forming composition comprises a total level of polymeric structurant in the fibrous element of from about 5% to 50% or less by weight on a dry fibrous element basis and/or dry particle basis and/or dry fibrous structure basis and a total level of active agents in the fibrous element of from 50% to about 95% by weight on a dry fibrous element basis and/or dry particle basis and/or dry fibrous structure basis.

In one example, the filament-forming composition may comprise any suitable total level of polymeric structurant and any suitable level of active agents so long as the fibrous element produced from the filament-forming composition comprises a total level of polymeric structurant in the fibrous element and/or particle of from about 5% to 50% or less by weight on a dry fibrous element basis and/or dry particle basis and/or dry fibrous structure basis and a total level of active agents in the fibrous element and/or particle of from 50% to about 95% by weight on a dry fibrous element basis and/or dry particle basis and/or dry fibrous structure basis, wherein the weight ratio of polymeric structurant to total level of surfactant and/or high melting point fatty compound is 1 or less.

In one example, the filament-forming composition comprises from about 1% and/or from about 5% and/or from about 10% to about 50% and/or to about 40% and/or to about 30% and/or to about 20% by weight of the filament-forming composition of polymeric structurant; from about 1% and/or from about 5% and/or from about 10% to about 50% and/or to about 40% and/or to about 30% and/or to about 20% by weight of the filament-forming composition of active agents; and from about 20% and/or from about 25% and/or from about 30% and/or from about 40% and/or to about 80% and/or to about 70% and/or to about 60% and/or to about 50% by weight of the filament-forming composition of a volatile solvent, such as water. The filament-forming composition may comprise minor amounts of other active agents, such as less than 10% and/or less than 5% and/or less than 3% and/or less than 1% by weight of the filament-forming composition of plasticizers, pH adjusting agents, and other active agents.

The filament-forming composition is spun into one or more fibrous elements and/or particles by any suitable spinning process, such as meltblowing, spunbonding, electro-spinning, and/or rotary spinning. In one example, the filament-forming composition is spun into a plurality of fibrous elements and/or particles by meltblowing. For example, the filament-forming composition may be pumped from a tank to a meltblown spinnerette. Upon exiting one or more of the filament-forming holes in the spinnerette, the filament-forming composition is attenuated with air to create one or more fibrous elements and/or particles. The fibrous elements and/or particles may then be dried to remove any remaining solvent used for spinning, such as the water.

The fibrous elements and/or particles of the present invention may be collected on a belt, such as a patterned belt to form a fibrous structure comprising the fibrous elements and/or particles.

Non-Limiting Examples for Making Fibrous Structures

The addition of particles may be accomplished during the formation of the embryonic fibers or after collection of the embryonic fibers on the patterned belts.

As shown in FIGS. 8 and 9, the fibrous elements of the present invention may be made as follows. Fibrous elements may be formed by means of a small-scale apparatus, a schematic representation of which is shown in FIGS. 8 and 9. A pressurized tank 62, suitable for batch operation is filled with a suitable filament-forming composition 48 for spinning A pump 64, such as a Zenith®, type PEP II, having a capacity of 5.0 cubic centimeters per revolution (cc/rev), manufactured by Parker Hannifin Corporation, Zenith Pumps division, of Sanford, N.C., USA may be used to facilitate transport of the filament-forming composition to a spinning die 50. The flow of the filament-forming composition 48 from the pressurized tank 62 to the spinning die 50 may be controlled by adjusting the number of revolutions per minute (rpm) of the pump 64. Pipes 66 are used to connect the pressurized tank 62, the pump 64, and the spinning die 50.

The spinning die 50 shown in FIG. 9 has several rows of circular extrusion nozzles (fibrous element-forming holes 52) spaced from one another at a pitch P of about 1.524 millimeters (about 0.060 inches). The nozzles have individual inner diameters of about 0.305 millimeters (about 0.012 inches) and individual outside diameters of about 0.813 millimeters (about 0.032 inches). Each individual nozzle is encircled by an annular and divergently flared orifice (concentric attenuation fluid hole 56 to supply attenuation air to each individual melt capillary 54. The filament-forming composition 48 extruded through the nozzles is surrounded and attenuated by generally cylindrical, humidified air streams supplied through the orifices.

Attenuation air can be provided by heating compressed air from a source by an electrical-resistance heater, for example, a heater manufactured by Chromalox, Division of Emerson Electric, of Pittsburgh, Pa., USA. An appropriate quantity of steam was added to saturate or nearly saturate the heated air at the conditions in the electrically heated, thermostatically controlled delivery pipe. Condensate was removed in an electrically heated, thermostatically controlled, separator.

The embryonic fibrous elements are cooled by a quenching air stream having a temperature from about 5° C. (about 40° F.) to about 15° C. (about 50° F.) by a water chiller (not shown) supplied through cooling nozzles and discharged at an angle of about 90 degrees relative to the general orientation of the embryonic fibers being extruded. The cooled and solidified embryonic fibrous elements are collected on a collection device, such as, for example, a movable foraminous belt or patterned collection belt. The addition of a vacuum source directly under the formation zone may be used to aid collection of the fibers.

Examples

The following are non-limiting examples of the conditioner compositions described herein. It will be appreciated that other modifications of the present invention within the skill of those in the art can be undertaken without departing from the spirit and scope of this invention. With respect to the examples that include particles, the particles may be added during the formation of the embryonic fibers. In the other examples, the liquid minors are added by spray coating. With the respect to the examples that have a liquid minors spray coating, the coating is applied according to our MATS liquid addition process.

All parts, percentages, and ratios herein are by weight unless otherwise specified. Some components may come from suppliers as dilute solutions. The amount stated reflects the weight percent of the active material, unless otherwise specified.

TABLE 1

Fibrous Conditioner Structures with Liquid Minors Spray Coating

| | Ex. 1 | Ex. 2 |
|---|---|---|
| Water | 1.73 | 1.89 |
| Behentrimonium Methosulfate[1] | 17.87 | 19.49 |
| Stearyl Alcohol[2] | 39.33 | 42.89 |
| Cetyl Alcohol[3] | 16.10 | 17.55 |
| Lauroyl Methyl Glucamide | 8.05 | 8.78 |
| Polyvinylpyrrolidone | 3.57 | 3.90 |
| Amodimethicone[4] | 7.85 | 0.00 |
| Perfume | 5.50 | 5.50 |
| Avg. Hand Dissolution Initial | 8 | 6 |
| Avg. Hand Dissolution after one week at 40° C. | 30 | 30 |

[1]Behentrimonium Methosulfate-IPA from Croda ™
[2]GlucoTain ® Clean RM from Clariant ™
[3]PVP K120 from Ashland ™
[4]Amodimethicone from Momentive ™ Performance Materials For Examples 1-2, the fibrous structures were formed and then a liquid spray containing perfume and optionally silicone was applied to the outer surface of the structures. The initial average hand dissolution was measured soon after the structures were made and the initial average hand dissolution values are relatively low. However, after one week of storage in sealed foil sachets at accelerated stability conditions (40° C. and 20% RH), the average hand dissolution scores for both Examples 1-2 were 30, which is generally not consumer acceptable.

The accelerated stability conditions are meant to mimic storage over the shelf life of the product, which generally includes shipping, handling, and storage in locations that are not climate controlled. The structures in Examples 1-2 may not be consumer acceptable over the shelf life of the product.

In Examples 1-2, the perfume interacted with at least one conditioner ingredient, forming waxy structures over time, which inhibit the dissolution of the substrate when exposed to water.

Since coating the structures with a liquid spray containing perfume did not produce a consumer acceptable substrate, the next step was to try putting the perfume into particles, including encapsulated particles. Table 2, below, includes three comparative examples of particles containing perfumes.

TABLE 2

Perfume Particles

| Ingredient | Ex. A | Ex. B | Ex. C |
|---|---|---|---|
| PEG-4000 | 80 | | |
| Polyacrylate Crosspolymer-9[1] | | | 87.5 |
| Polyvinyl Alcohol[2] | | | 0.80 |
| Xanthum Gum | | | 0.20 |
| Sodium Benzoate | | | 0.25 |
| Potassium Sorbate | | | 0.25 |
| Hydroxyethyl Cellulose | | 0.95 | |
| Hi-Cap ® Starch[3] | | 42.58 | |
| Lakeland PA-900 | | 5.24 | |
| Calcium Acetate Hydrate | | 5.24 | |
| Citric Acid | | 1.83 | |
| Perfume #1 | 20 | | |
| Perfume #2 | | 44.16 | |
| Perfume #3 | | | 11.0 |
| % Leakage | 49.45 +/- 0.70 | 9.66 +/- 0.24 | 5.71 +/- 0.14 |

[1]Polyacrylate Crosspolymer-9 from Spray-Tek ®
[2]Kuraray Poval ® commercially available from Kuraray ™
[3]Hi-Cap ® 100 from Ingredion ™

The % leakage was determined after storing the particle powder at 40° C. and 20% RH overnight, using the Analysis of Free Perfume in Perfume Particles, hereinafter. Example A had a leakage of 49.45% and the particles appeared oily and wet and therefore Example A was not added to a structure. Examples B and C had a % leakage of less than 10% and therefore these perfume particles were tested in structures, see Table 3, below. In Example B the perfume particles are a matrix and in Example C the perfume is contained in an encapsulated particle.

TABLE 3

Fibrous Conditioner Structures with Perfume Particles

| | Ex. 3 | Ex. 4 |
|---|---|---|
| Water | 1.67 | 1.11 |
| Behentrimonium Methosulfate[1] | 17.27 | 11.45 |
| Stearyl Alcohol | 38.00 | 24.39 |
| Cetyl Alcohol | 15.55 | 9.98 |

TABLE 3-continued

Fibrous Conditioner Structures with Perfume Particles

| | Ex. 3 | Ex. 4 |
|---|---|---|
| Lauroyl Methyl Glucamide[2] | 7.77 | 4.99 |
| Polyvinylpyrrolidone[3] | 3.45 | 2.22 |
| Particles from Table 2 | 16.28 | 45.86 |
| | Ex. B | Ex. C |
| Avg. Hand Dissolution Initial | 13 | 9 |
| Avg. Hand Dissolution after one week at 40° C. | 30 | 25 |

[1]Behentrimonium Methosulfate-IPA from Croda ™
[2]GlucoTain ® Clean RM from Clariant ™
[3]PVP K120 from Ashland ™

For Examples 3-4, the particles were added throughout the fibrous structures as described herein. The initial average hand dissolution values are relatively low, however, after one week at accelerated stability conditions (40° C. and 20% RH), the average hand dissolution scores for both Examples 3-4 were too high to be generally considered consumer acceptable.

Figure 10B:
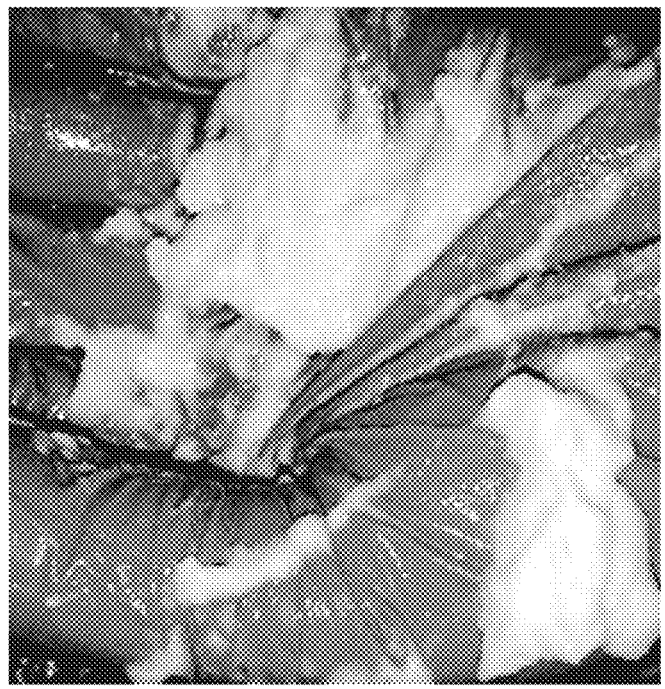
FIG. 10B is a photograph of the fibrous structure of Example 3 after water is applied.
Figure 10A:
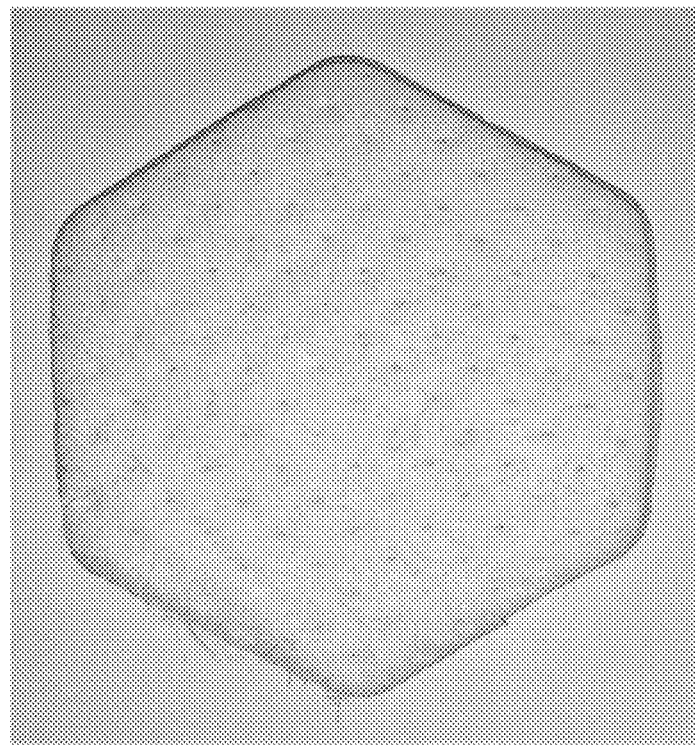
FIG. 10A is a photograph of the fibrous structure of Example 3.

FIG. 10A is a photograph of the fibrous structure of Example 3. The apertures are at least partially obstructed by waxy structures in the fibrous structure. FIG. 10B is a photograph of the structure after water is applied. Instead of forming a creamy conditioner, the fibrous structure dissolves into a clumpy paste that would be difficult to easily distribute across a user's hair.

While not willing to be bound be theory, it is believed that in perfume microcapsules (PMC), like Example 4, if the encapsulated layer is fractured or otherwise compromised, the encapsulated perfume oil can leak out and interact with the conditioner ingredients in the structure.

TABLE 4

Perfume Particles

| | Ex. D | Ex. E |
|---|---|---|
| PEG-8000 | 80 | |
| PMC[1] | 20 | |
| B-cyclodextrin[2] | | 93 |
| Perfume #7 | | 7 |
| % Leakage | 0.64 ± 0.04 | 0.04 ± 0.002 |

[1]Supplied by Encapsys Inc.
[2]Supplied by Wacker ™

Examples D and E had low leakage and could probably be added to a fibrous structure without causing waxy structures to form over time. In Example D, the PMCs are combined with PEG 8000 to form a particle. A fibrous structure with conditioner actives and Example D is in Table 6, hereafter.

The particle in Example E, may be added to the fibrous structure and it may have acceptable dissolution. However, the concentration of perfume is low and too many particles may have to be added to the fibrous structure to get a consumer noticeable scent.

TABLE 5

Matrix Particles with Perfume

| | Ex. F | Ex. G | Ex. H | Ex. I | Ex. J | Ex. K |
|---|---|---|---|---|---|---|
| Envicap ™ Crosslinked Starch[1] | 57.0 | 57.0 | 57.0 | 57.0 | 57.0 | 57.0 |
| Perfume #1 | 43.0 | | | | | |
| Perfume #2 | | 43.0 | | | | |
| Perfume #3 | | | 43.0 | | | |

TABLE 5-continued

| Matrix Particles with Perfume | | | | | | |
|---|---|---|---|---|---|---|
| | Ex. F | Ex. G | Ex. H | Ex. I | Ex. J | Ex. K |
| Perfume #4 | | | | 43.0 | | |
| Perfume #5 | | | | | 43.0 | |
| Perfume #6 | | | | | | 43.0 |
| % Leakage | 0.13 ± 0.003 | 1.21 ± 0.09 | 0.07 ± 0.003 | 0.09 ± 0.0004 | 0.09 ± 0.04 | 0.04 ± 0.01 |

[1]31523 Corn Starch/Maltodextrin Crosspolymer from TruCapSol ™
2. Kuraray Poval ™ commercially available from Kuraray Examples F-K each had a different perfume and they all had low % leakage. Therefore, it may be possible to add these to fibrous structures that have consumer acceptable average hand dissolution levels. See Table 6, hereafter, for examples of fibrous structures with some of these particles.

TABLE 6

| Fibrous Structures with Perfume Particles | | | |
|---|---|---|---|
| Ingredient | Ex. 5 | Ex. 6 | Ex. 7 |
| Water | 1.67 | 1.67 | 1.35 |
| Behenyltrimonium Methosulfate[1] | 17.21 | 17.21 | 13.60 |
| Cetyl Alcohol | 15.49 | 15.49 | 13.25 |
| Stearyl Alcohol | 37.86 | 37.86 | 30.85 |
| Lauroyl Methyl Glucamide [2] | 7.744 | 7.744 | 6.1 |
| Polyvinylpyrrolidone, K120[3] | 3.44 | 3.44 | 2.75 |
| Particles from Table 4 | | | 6.42 Ex. D |
| Particles from Table 5 | 14.94 Ex. K | 14.94 Ex. F | |
| Polyvinylpyrrolidone, K30[4] | 1.66 | 1.66 | |
| Avg. Hand Dissolution Initial | 7.3 | 5.3 | 5 |
| Avg. Hand Dissolution after one week 40° C. | 12.0 | 8.3 | 10 |

[1]Behentrimonium Methosulfate-IPA from Croda ™
[2] GlucoTain ® Clean RM from Clariant ™
[3]PVP K120 from Ashland ™
[4]Amodimethicone from Momentive ™ Performance Materials Examples 5-6 contain matrix particles. The average hand dissolution after one week at 40° C. can be acceptable to consumers.

Example 7 is a fibrous structure that contains PMCs that are coated in PEG-8000. It is interesting to note that making a matrixed particle with perfume and PEG, including PEG-4000 (see Table 1) and even PEG-8000, may not produce particles that can be incorporated into a fibrous structure that is consumer acceptable. When PMCs are incorporated into the fibrous structures, the average hand dissolution is not consumer acceptable (see Table 3). However, when the particles contain PMC and PEG, the leakage is low and the structure can have an acceptable average hand dissolution rate.

The Examples in Table 7 are conditioner Example 3 (see Table 3) and Examples 9 and 10 include perfume matrix particles. The perfume matrix particles have a matrix material that can include a naturally derived starch or maltodextrin and in examples 9 and 10, the matrix material is free of a crosslinking material and therefore, the matrix material is not crosslinked. The perfume matrix particles are agglomerated, as described herein, and the agglomerates are 300 μm to 400 μm. The agglomerates are added to the webs.

TABLE 7

| | | Particle add-on level Particle:Fiber ratio wt:wt | Avg. Hand Dissolution Initial | Perfume Intensity Score when wet |
|---|---|---|---|---|
| Ex. 8 | Ex. 3 Conditioner (nil perfume) | 0 | 4 | 0 |
| Ex. 9 | Ex. 3 Conditioner + perfume particles (lower level) | 0.24 | 5 | 60 |
| Ex. 10 | Ex. 3 Conditioner + perfume particles (higher level) | 0.48 | 7 | 75 |

Examples 8-10 all have consumer acceptable hand dissolution scores. In Table 7, the perfume intensity score was determined for each composition by a panel assessment in which each conditioner composition is given an intensity score on a scale of 0 to 100, 100 being very strong. The inclusion of perfume particles dramatically increases the perfume intensity of the wet product. The perfume in Examples 9 and 10 blooms when wet, which may be consumer accepted.

Test Methods

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 2 hours prior to the test. The samples tested are "usable units." "Usable units" as used herein means sheets, flats from roll stock, pre-converted flats, and/or single or multi-ply products. All tests are conducted under the same environmental conditions and in such conditioned room. Do not test samples that have defects such as wrinkles, tears, holes, and like. Samples conditioned as described herein are considered dry samples (such as "dry filaments") for testing purposes. All instruments are calibrated according to manufacturer's specifications.

Basis Weight Test Method

Basis weight of a fibrous structure is measured on stacks of twelve usable units using a top loading analytical balance with a resolution of ±0.001 g. The balance is protected from air drafts and other disturbances using a draft shield. A precision cutting die, measuring 3.500 in ±0.0035 in by 3.500 in ±0.0035 in is used to prepare all samples.

With a precision cutting die, cut the samples into squares. Combine the cut squares to form a stack twelve samples thick. Measure the mass of the sample stack and record the result to the nearest 0.001 g.

The Basis Weight is calculated in lbs/3000 ft² or g/m² as follows:

Basis Weight=(Mass of stack)/[(Area of 1 square in stack)×(No. of squares in stack)]

For example,

Basis Weight (lbs/3000 ft²)=[[Mass of stack (g)/ 453.6 (g/lbs)]/[12.25 (in²)/144 (in²/ft²)×12]]× 3000 or,

Basis Weight (g/m²)=Mass of stack (g)/[79.032 (cm²)/10,000 (cm²/m²)×12]

Report result to the nearest 0.1 lbs/3000 ft² or 0.1 g/m². Sample dimensions can be changed or varied using a similar precision cutter as mentioned above, so as at least 100 square inches of sample area in stack.

Water Content Test Method

The water (moisture) content present in a fibrous element and/or particle and/or fibrous structure is measured using the following Water Content Test Method. A fibrous element and/or particle and/or fibrous structure or portion thereof ("sample") in the form of a pre-cut sheet is placed in a conditioned room at a temperature of 23° C.±1.0° C. and a relative humidity of 50%±2% for at least 24 hours prior to testing. Each fibrous structure sample has an area of at least 4 square inches, but small enough in size to fit appropriately on the balance weighing plate. Under the temperature and humidity conditions mentioned above, using a balance with at least four decimal places, the weight of the sample is recorded every five minutes until a change of less than 0.5% of previous weight is detected during a 10 minute period. The final weight is recorded as the "equilibrium weight". Within 10 minutes, the samples are placed into the forced air oven on top of foil for 24 hours at 70° C.±2° C. at a relative humidity of 4%±☐2% for drying. After the 24 hours of drying, the sample is removed and weighed within 15 seconds. This weight is designated as the "dry weight" of the sample.

The water (moisture) content of the sample is calculated as follows:

$$\% \text{ Water in sample} = 100\% \times \frac{\text{(Equilibrium weight of sample} - \text{Dry weight of sample)}}{\text{Dry weight of sample}}$$

The % Water (moisture) in sample for 3 replicates is averaged to give the reported % Water (moisture) in sample. Report results to the nearest 0.1%.

Median Particle Size Test Method

This test method must be used to determine median particle size.

The median particle size test is conducted to determine the median particle size of the seed material using ASTM D 502-89, "Standard Test Method for Particle Size of Soaps and Other Detergents", approved May 26, 1989, with a further specification for sieve sizes used in the analysis. Following section 7, "Procedure using machine-sieving method," a nest of clean dry sieves containing U.S. Standard (ASTM E 11) sieves #8 (2360 um), #12 (1700 um), #16 (1180 urn), #20 (850 um), #30 (600 um), #40 (425 um), #50 (300 um), #70 (212 um), #100 (150 um) is required. The prescribed Machine-Sieving Method is used with the above sieve nest. The seed material is used as the sample. A suitable sieve-shaking machine can be obtained from W.S. Tyler Company of Mentor, Ohio, U.S.A.

The data are plotted on a semi-log plot with the micron size opening of each sieve plotted against the logarithmic abscissa and the cumulative mass percent ($Q_3$) plotted against the linear ordinate. An example of the above data representation is given in ISO 9276-1:1998, "Representation of results of particle size analysis—Part 1: Graphical Representation", Figure A.4. The seed material median particle size ($D_{50}$), for the purpose of this invention, is defined as the abscissa value at the point where the cumulative mass percent is equal to 50 percent, and is calculated by a straight line interpolation between the data points directly above (a50) and below (b50) the 50% value using the following equation:

$$D_{50}=10\char`\^[\text{Log}(D_{a50})-(\text{Log}(D_{a50})-\text{Log}(D_{b50}))*(Q_{a50}-50\%)/(Q_{a50}-Q_{b50})]$$

where $Q_{a50}$ and $Q_{b50}$ are the cumulative mass percentile values of the data immediately above and below the $50^{th}$ percentile, respectively; and $D_{a50}$ and $D_{b50}$ are the micron sieve size values corresponding to these data.

In the event that the 50th percentile value falls below the finest sieve size (150 um) or above the coarsest sieve size (2360 um), then additional sieves must be added to the nest following a geometric progression of not greater than 1.5, until the median falls between two measured sieve sizes.

The Distribution Span of the Seed Material is a measure of the breadth of the seed size distribution about the median. It is calculated according to the following:

$$\text{Span}=(D_{84}/D_{50}+D_{50}/D_{16})/2$$

Where $D_{50}$ is the median particle size and $D_{84}$ and $D_{16}$ are the particle sizes at the sixteenth and eighty-fourth percentiles on the cumulative mass percent retained plot, respectively.

In the event that the $D_{16}$ value falls below the finest sieve size (150 um), then the span is calculated according to the following:

$$\text{Span}=(D_{84}/D_{50}).$$

In the event that the $D_{84}$ value falls above the coarsest sieve size (2360 um), then the span is calculated according to the following:

$$\text{Span}=(D_{50}/D_{16}).$$

In the event that the $D_{16}$ value falls below the finest sieve size (150 um) and the $D_{84}$ value falls above the coarsest sieve size (2360 um), then the distribution span is taken to be a maximum value of 5.7.

Thickness Method

Thickness of a fibrous structure is measured by cutting 5 samples of a fibrous structure sample such that each cut sample is larger in size than a load foot loading surface of a VIR Electronic Thickness Tester Model II available from Thwing-Albert Instrument Company, Philadelphia, Pa. Typically, the load foot loading surface has a circular surface area of about 3.14 in². The sample is confined between a horizontal flat surface and the load foot loading surface. The load foot loading surface applies a confining pressure to the sample of 15.5 g/cm². The thickness of each sample is the resulting gap between the flat surface and the load foot loading surface. The thickness is calculated as the average thickness of the five samples. The result is reported in millimeters (mm).

Shear Viscosity Test Method

The shear viscosity of a filament-forming composition of the present invention is measured using a capillary rheometer, Goettfert Rheograph 6000, manufactured by Goettfert USA of Rock Hill S.C., USA. The measurements are conducted using a capillary die having a diameter D of 1.0 mm and a length L of 30 mm (i.e., L/D=30). The die is attached to the lower end of the rheometer's 20 mm barrel, which is held at a die test temperature of 75° C. A preheated to die test temperature, 60 g sample of the filament-forming composition is loaded into the barrel section of the rheometer. Rid the sample of any entrapped air. Push the sample from the barrel through the capillary die at a set of chosen rates 1,000-10,000 seconds$^{-1}$. An apparent shear viscosity can be calculated with the rheometer's software from the pressure drop the sample experiences as it goes from the barrel through the capillary die and the flow rate of the sample through the capillary die. The log (apparent shear viscosity) can be plotted against log (shear rate) and the plot can be fitted by the power law, according to the formula $\eta=K\gamma^{n-1}$, wherein K is the material's viscosity constant, n is the material's thinning index and $\gamma$ is the shear rate. The reported apparent shear viscosity of the filament-forming composition herein is calculated from an interpolation to a shear rate of 3,000 sec$^{-1}$ using the power law relation.

Diameter Test Method

The diameter of a discrete fibrous element or a fibrous element within a fibrous structure is determined by using a Scanning Electron Microscope (SEM) or an Optical Microscope and an image analysis software. A magnification of 200 to 10,000 times is chosen such that the fibrous elements are suitably enlarged for measurement. When using the SEM, the samples are sputtered with gold or a palladium compound to avoid electric charging and vibrations of the fibrous element in the electron beam. A manual procedure for determining the fibrous element diameters is used from the image (on monitor screen) taken with the SEM or the optical microscope. Using a mouse and a cursor tool, the edge of a randomly selected fibrous element is sought and then measured across its width (i.e., perpendicular to fibrous element direction at that point) to the other edge of the fibrous element. A scaled and calibrated image analysis tool provides the scaling to get actual reading in μm. For fibrous elements within a fibrous structure, several fibrous element are randomly selected across the sample of the fibrous structure using the SEM or the optical microscope. At least two portions of the fibrous structure are cut and tested in this manner Altogether at least 100 such measurements are made and then all data are recorded for statistical analysis. The recorded data are used to calculate average (mean) of the fibrous element diameters, standard deviation of the fibrous element diameters, and median of the fibrous element diameters.

Another useful statistic is the calculation of the amount of the population of fibrous elements that is below a certain upper limit. To determine this statistic, the software is programmed to count how many results of the fibrous element diameters are below an upper limit and that count (divided by total number of data and multiplied by 100%) is reported in percent as percent below the upper limit, such as percent below 1 micrometer diameter or %-submicron, for example. We denote the measured diameter (in μm) of an individual circular fibrous element as di.

In the case that the fibrous elements have non-circular cross-sections, the measurement of the fibrous element diameter is determined as and set equal to the hydraulic diameter which is four times the cross-sectional area of the fibrous element divided by the perimeter of the cross-section of the fibrous element (outer perimeter in case of hollow fibrous elements). The number-average diameter, alternatively average diameter is calculated as:

$$d_{num} = \frac{\sum_{i=1}^{n} d_i}{n}$$

Fibrous Element Composition Test Method

In order to prepare fibrous elements for fibrous element composition measurement, the fibrous elements must be conditioned by removing any coating compositions and/or materials present on the external surfaces of the fibrous elements that are removable. An example of a method for doing so is washing the fibrous elements 3 times with a suitable solvent that will remove the external coating while leaving the fibrous elements unaltered. The fibrous elements are then air dried at 23° C.±1.0° C. until the fibrous elements comprise less than 10% moisture. A chemical analysis of the conditioned fibrous elements is then completed to determine the compositional make-up of the fibrous elements with respect to the filament-forming materials and the active agents and the level of the filament-forming materials and active agents present in the fibrous elements.

The compositional make-up of the fibrous elements with respect to the filament-forming material and the active agents can also be determined by completing a cross-section analysis using TOF-SIMs or SEM. Still another method for determining compositional make-up of the fibrous elements uses a fluorescent dye as a marker. In addition, as always, a manufacturer of fibrous elements should know the compositions of their fibrous elements.

Lamellar Structure Test Method

The Lamellar Structure Test Method makes use of small-angle x-ray scattering (SAXS) to determine if a lamellar structure is present in an dissolvable solid structure either in a conditioned, dry state or upon wetting after having been previously in a conditioned, dry state. Dissolvable solid structure are conditioned at a temperature of 23° C.±2.0° C. and a relative humidity of 40%±10% for a minimum of 12 hours prior to the test. Dissolvable solid structure conditioned as described herein are considered to be in a conditioned, dry state for the purposes of this invention. All instruments are calibrated according to manufacturer's specifications.

Dry Sample Preparation

To prepare a sample to be analyzed directly in the conditioned, dry state, a specimen of about 1.0 cm diameter disc is isolated from the center of a dissolvable solid structure and is loaded into a conventional SAXS solid sample holder with aperture diameter between 4 and 5 mm (Multiple specimen discs may be extracted from multiple dissolvable solid structures and stacked, if necessary, to ensure sufficient scattering cross-section.) The loaded sample holder is immediately placed in the appropriate instrument for data collection.

Wet Sample Preparation

Three samples are analyzed upon wetting from the dry, conditioned state. Specimens are extracted from dry, conditioned dissolvable solid structure and hydrated with water in order to achieve three separate preparations each possessing a different material-to-water mass ratio. The three different material-to-water mass ratios to be prepared are 1:5; 1:9; and 1:20. For each mass ratio, one or more specimens (as needed) 1 cm in diameter are extracted from the geometric centers of one or more dissolvable solid structure in the dry, conditioned state are hydrated with 23° C.±2.0° C. filtered deionized (DI) water in order to achieve the intended material-to-water mass ratio. Each of the three material/water mixtures (each corresponding to a different mass ratio) is stirred under low shear gently by hand at room temperature using a spatula until visibly homogenous. Each material/water mixture is then immediately loaded into a separate quartz capillary tube with outer diameter 2.0 mm in diameter and 0.01 mm wall thickness. The capillary tubes are immediately sealed with a sealant such as an epoxy resin to prevent the evaporation of water from the preparations. The sealant is permitted to dry for at least 2 hours and until dry at a temperature of 23° C.±2.0° C. prior to sample analysis. Each prepared wet sample is introduced into an appropriate SAXS instrument and data are collected.

Testing and Analysis

Samples are tested using SAXS in 2-dimension (2D) transmission mode over an angular range in of 0.3° to 3.0° 2θ, to observe the presence and spacing of any intensity bands in the x-ray scatter pattern. The test is conducted using a SAXS instrument (such as the NanoSTAR, Bruker AXS Inc., Madison, Wis., U.S.A., or equivalent). Conditioned, dry samples are analyzed under ambient pressure. Sealed liquid samples are analyzed in the instrument under vacuum. All samples are analyzed at a temperature of 23° C.±2.0° C. The x-ray tube of the instrument is operated sufficient power to ensure that any scattering bands present are clearly detected. The beam diameter is 550±50 μm. One suitable set of operating conditions includes the following selections: NanoSTAR instrument; micro-focus Cu x-ray tube; 45 kV and 0.650 mA power; Vantec2K 2-Dimensional area detector; collection time of 1200 seconds; and distance between the sample and detector of 112.050 cm. The raw 2-D SAXS scattering pattern is integrated azimuthally to determine intensity (I) as a function of the scattering vector (q), which are expressed throughout this method units of reciprocal angstroms ($Å^{-1}$). The values for q are calculated by the SAXS instrument according to the following equation:

$$q = \frac{4\pi}{\lambda} \sin\theta$$

where:
2θ is the scattering angle; and
λ is the wavelength used.

For each integrated SAXS analyzed, the value of q in $Å^{-1}$ corresponding to each intensity peak on the plot of I vs q is identified and recorded from smallest to largest. (One of skill in the art knows that a sharp peak in q near the origin corresponds to scatter off of the beam stop and is disregarded in this method.) The value of q corresponding to the first intensity peak (the lowest value of q) is referred to as q*.

For a sample analyzed directly in the dry, conditioned state, if an intensity peak is present at 2q*±0.002 $Å^{-1}$, the sample is determined to exhibit a lamellar structure, and the characteristic d-spacing parameter is defined as 2π/q*. If no intensity peak if present at 2q*±0.002 $Å^{-1}$, the sample analyzed directly in the dry, conditioned state is determined to not exhibit a lamellar structure.

For a sample analyzed upon wetting from the dry, conditioned state, if an intensity peak is present at 2q*±0.002 $Å^{-1}$, the sample is determined to exhibit a lamellar structure, and the characteristic d-spacing parameter is defined as 2π/q*. If no intensity peak is present at 2q*±0.002 $Å^{-1}$, the sample is determined to not exhibit a lamellar structure. If a lamellar structure is determined to be present in at least any one of the three material/water ratios prepared, then this material is determined to exhibit a lamellar structure upon wetting. If no intensity peak is present at 2q*±0.002 $Å^{-1}$, in any of the three material/water ratios prepared, the material is determined to not exhibit a lamellar structure upon wetting.

Hand Dissolution Method

Materials Needed:

Fibrous structures to be tested: 3-5 fibrous structures (finished product samples) are tested so that an average of the number of strokes for each if the individual fibrous structure samples is calculated and recorded as the Average Hand Dissolution value for the fibrous structure. For this method, the entire consumer saleable or consumer use fibrous structure is tested. If the entire consumer saleable or consumer use fibrous structure has a footprint greater than 50 $cm^2$, then first cut the fibrous structure to have a footprint of 50 $cm^2$.

Nitrile Gloves
10 cc syringe
Plastic Weigh boat (~3 in×3 in)
100 mL Glass beaker
Water (City of Cincinnati Water or equivalent having the following properties: Total Hardness=155 mg/L as $CaCO_2$; Calcium content=33.2 mg/L; Magnesium content=17.5 mg/L; Phosphate content=0.0462 mg/L). Water used is water 7 grains per gallon (gpg) hardness and 40° C.+/−5° C.

Protocol:
Add 80 mL of water to glass beaker.
Heat water in beaker until water is at a temperature of 40° C.+/−5° C.
Transfer 15 mL of the water from the beaker into the weigh boat via the syringe.
Within 10 seconds of transferring the water to the weigh boat, place fibrous structure sample in palm of gloved hand (hand in cupped position in non-dominant hand to hold fibrous structure sample).
Using dominant hand, add water quickly from the weigh boat to the fibrous structure sample and allow to immediately wet for a period of 5-10 seconds.
Rub with opposite dominant hand (also gloved) in 2 rapid circular strokes.
Visually examine the fibrous structure sample in hand after the 2 strokes. If fibrous structure sample is completely dissolved, record number of strokes=2 Dissolution Strokes. If not completely dissolved, rub remaining fibrous structure sample for 2 more circular strokes (4 total) and observe degree of dissolution. If the fibrous structure sample contains no solid pieces after the 2 additional strokes, record number of strokes=4 Dissolution Strokes. If after the 4 strokes total, the fibrous structure sample still contains solid pieces of un-dissolved fibrous structure sample, continue rubbing remaining fibrous structure sample in additional 2 circular strokes and check if there are any remaining solid pieces of fibrous structure sample after each additional 2 strokes until fibrous structure sample is completely dissolved or until reaching a total of 30 strokes, whichever comes first. Record the total number of strokes. Record 30 Dissolution Strokes even if solid fibrous structure sample pieces remain after the maximum of 30 strokes.
Repeat this process for each of the additional 4 fibrous structure samples.

Calculate the arithmetic mean of the recorded values of Dissolution Strokes for the 5 individual fibrous structure samples and record as the Average Hand Dissolution Value for the fibrous structure. The Average Hand Dissolution Value is reported to the nearest single Dissolution Stroke unit.

Analysis of Free Perfume in Perfume Particles

All laboratory instruments should be operated according to manufacturers' instructions, as set forth in the instrument operation manuals and instructional materials, unless otherwise indicated.

Apparatus
1. Laboratory Timer.
2. HT Tully® membrane filter, Schwartz, Twin Rivers, Wis., USA
3. Gas Chromatograph (GC): Agilent model 6890 or equivalent
4. GC column: Agilent DB-SMS, 30 M×0.250 mm ID, 1.0 μm film thickness obtained from Agilent Technologies, Inc. Wilmington, Del., USA.
5. Carrier gas, helium, 1.2 ml/min. flow rate.
6. The Detector is a model Agilent 5973 Mass Selective Detector (or equivalent) obtained from Agilent Technologies, Inc., Wilmington, Del., USA having a source temperature of about 230° C., and a MS Quad temperature of about 150° C.

Sample Preparation
7. After storing the particles at 40° C. overnight, place 0.2 g of perfume particles into the bottom of a 20 mL glass vial (minimizing product on sides or top of vial).
8. To this vial add 10 mL of hexane.
9. Using a touch vortexing unit, vortex sample for 10 seconds (if large amounts of product are still agglomerated to the bottom, vortex for another 10 seconds).
10. Then mix using a roller mixer for 5 minutes.
11. Using a syringe and nylon syringe filter with a 0.45 μm HT Tully® Membrane filter (if it is clear, no filter needed) 1.5 mL of the clear hexane layer into a 2 mL GC vial. Cap vial tightly.
12. A 2 μL aliquot of each sample will then be analyzed by GC/MS.
13. All samples are analyzed in triplicate (n=2).

Analysis
1. Transfer sample vials to proper sample tray and proceed with GC-MS analysis.
2. Start sequence of sample loading and analysis. In this step, the GC-MS analysis run is in split mode with split ratio 10:1. The following temperature program is used: an initial temperature of about 75° C.
   increase the initial temperature at a rate of about 6° C./min until a temperature of 280° C. is reached, then hold for 3.83 minutes. The total run time is 38 minutes.
3. Perfume compounds are identified using the MS spectral libraries of John Wiley & Sons (Wiley 10) and the National Institute of Standards and Technology (NIST 08), purchased and licensed through Agilent Technologies, Inc., Wilmington, Del., USA.
4. Chromatographic peaks for specific ions are integrated using the Chemstation software (version E) obtained from Agilent Technologies, Inc., Wilmington, Del., USA.
5. Use the perfume standard and prepare it according to the method described herein and perform the GC-MS analysis, analyze the peaks, and integrate using the Chemstation software, as described herein.
6. Construct a calibration curve using peak area vs. known amount of the perfume to obtain a linear curve.
7. Calculate the corresponding perfume amount from the peak area of the hexane extracted free perfume from the test sample by using the linear.
8. The percent of free oil in the test sample is the amount of the free perfume (from step 7) over the total perfume in the sample (encapsulated amount).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A fibrous structure comprising:
   a) a plurality of fibrous elements comprising:
      i) a polymeric structurant having a weight average molecular weight of from about 10,000 to about 6,000,000 g/mol;
      ii) a high melting point fatty material having a carbon chain length C12-C22 or mixtures thereof, wherein the melting point is above 25° C.; and
      iii) a cationic surfactant;
   b) a plurality of perfume matrix particles comprising:
      i) from about 10% to about 70%, by weight of the matrix particle, perfume;
      ii) from about 30% to about 90%, by weight of the matrix particle, one or more water-soluble matrix materials;
      wherein the one or more water-soluble matrix materials comprise polysaccharide, polyvinyl alcohol, polyvinyl pyrrolidone and its copolymers, polyvinyloxazolidone, polystyrene sulfonate, vinyl caprolactam, vinyl valerolactam, vinyl imidazole, polyethylene glycol, polyacrylic acid, polymethacrylic acid, polyvinyl formamide, polyvinyl amine, polyacrylamides and modified polyacrylamides, polydimethylacrylamide and modified polydimethylacrylamides, polyvinyl methyl ether and its copolymers with maleic anhydride, maltodextrin, hydroxypropylmethyl cellulose, hydroxyethyl cellulose, hydroxypropyl cellulose, car- boxymethyl cellulose, hemicellulose derivatives, hydroxymethyl cellulose, or a combination thereof;

wherein the perfume matrix particles have a leakage of less than 5% according to the Analysis of Free Perfume in Perfume Particles;

wherein upon addition of water the fibrous structure forms a homogenous cream conditioner comprising a gel matrix and the perfume is released from the matrix particle.

2. The fibrous structure of claim 1, wherein the fibrous structure comprises an average hand dissolution score after one week at 40° C. of less than or equal to 15 according to the Hand Dissolution Method.

3. The fibrous structure of claim 1, wherein the matrix particles have a leakage of less than or equal to 2% according to the Analysis of Free Perfume in Perfume Particles.

4. The fibrous structure of claim 1, wherein the matrix particle comprises from about from about 20% to about 50%, by weight of the matrix particle, perfume.

5. The fibrous structure of claim 1, wherein the matrix particle comprises from about 40% to about 85%, by weight of the matrix particle, matrix materials.

6. The fibrous structure of claim 1, wherein the one or more water-soluble matrix materials comprising a polysaccharide comprising modified corn starch, dextrins, gum arabic, xanthan gum, gellan gum, pectin gum, konjac gum carboxyalkyl cellulose, or a combination thereof.

7. The fibrous structure of claim 6, wherein the matrix particle further comprising from about 1% to about 10%, by weight of the matrix particle, a crosslinking agent comprising dimethyldihydroxy urea, dimethyloldihhyrodyethylene urea, dimethylol urea, dihydroxyethylene urea, dimethylolethylene urea, dimethyldihydroxyethylene urea, citric acid, tartaric acid, malic acid, succinic acid, glutaric acid, citraconic acid, itaconic acid, tartrate monosuccinic acid, maleic acid, poly(methacrylic acid), poly(maleic acid), poly(methylvinylether-co-maleate) copolymer, copolymers of acrylic acid and copolymers of maleic acid, or a combination thereof.

8. The fibrous structure of claim 1, wherein the perfume matrix particles are agglomerated with one or more particles having a different benefit agent selected from effervescent agents, silicones, surfactants, cationic polymers, antimicrobials including antibacterials and antifungals, vitamin oils, vegetable oils, and combinations thereof.

9. The fibrous structure of claim 1, wherein the perfume matrix particles are agglomerated with one or more perfume matrix particles.

10. The fibrous structure of claim 1 wherein the fibrous elements are water-soluble.

11. The fibrous structure of claim 1, wherein the fibrous elements are substantially free of perfume.

12. The fibrous structure of claim 1, wherein the polymeric structurant is selected from pullulan, hydroxypropylmethyl cellulose, hydroxyethyl cellulose, hydroxypropyl cellulose, polyvinyl pyrrolidone, polyvinyl pyrrolidone-vinyl acetate copolymers, modified polyvinyl pyrrolidone, carboxymethyl cellulose, sodium alginate, xanthan gum, tragacanth gum, guar gum, acacia gum, Arabic gum, polyacrylic acid, methylmethacrylate copolymer, carboxyvinyl polymer, dextrin, pectin, chitin, levan, elsinan, collagen, gelatin, zein, gluten, soy protein, casein, polyvinyl alcohol, carboxylated polyvinyl alcohol, sulfonated polyvinyl alcohol, starch, starch derivatives, hemicellulose derivatives, proteins, chitosan, chitosan derivatives, polyethylene glycol, tetramethylene ether glycol, hydroxymethyl cellulose, and mixtures thereof.

13. The fibrous structure of claim 1, wherein at least one of the fibrous elements exhibits an average diameter of less than 50 μm as measured according to the Diameter Test Method.

14. The fibrous structure of claim 1, wherein a lamellar structure is formed upon addition of water to the dissolvable solid structure in the ratio of about 5:1.

15. The fibrous structure of claim 1, comprising from about 1 wt % to about 30 wt % of the polymeric structurant; wherein the polymeric structurant comprises selected from polyvinylpyrrolidone, polyvinylpyrrolidone copolymer, alkylated vinyl pyrrolidone, vinyl caprolactam, vinyl valerolactam, vinyl imidazole, acrylic acid, methacrylate, acrylamide, methacrylamide, dimethacrylamide, alkylaminomethacrylate, and alkylaminomethacrylamide monomers, or a combination thereof.

16. The fibrous structure of claim 1, having from about 20 wt % to about 40 wt % of cationic surfactant comprising quaternized ammonium salt, tertiary amine, polydimethylacrylamide, polydimethylacrylamide copolymer, stearamidopropyldimethylamine, or a combination thereof.

17. The fibrous structure of claim 1, wherein the high melting point fatty compound comprises a fatty alcohol and a blend of one or more fatty alcohols.

18. The fibrous structure of claim 1, wherein the particles can be free of and/or substantially free of a silica flow aid.

19. The fibrous structure of claim 1, wherein the water-soluble matrix material is substantially free of a crosslinking agent.

20. The fibrous structure of claim 19, wherein the one or more water-soluble matrix materials comprises polyvinyl alcohol, polyvinyl pyrrolidone, polyethylene oxide, or a combination thereof.

* * * * *